(12) United States Patent
Eibel

(10) Patent No.: US 10,201,577 B2
(45) Date of Patent: Feb. 12, 2019

(54) COMPOSITIONS AND METHODS FOR ENHANCING WORKING AND LONG-TERM MEMORY SUPPORT USING NEW COMBINATION OF GINKGO BILOBA AND PANAX GINSENG AND ASSOCIATED COMPONENTS

(71) Applicant: KEYVIEW LABS, INC., Tampa, FL (US)

(72) Inventor: Scott Eibel, Tampa, FL (US)

(73) Assignee: KEYVIEW LABS, INC., Tampa, FL (US)

( * ) Notice: Subject to any disclaimer, the term of this patent is extended or adjusted under 35 U.S.C. 154(b) by 0 days.

(21) Appl. No.: 15/431,833

(22) Filed: Feb. 14, 2017

(65) Prior Publication Data

US 2018/0228855 A1    Aug. 16, 2018

(51) Int. Cl.
```
A61K 36/00      (2006.01)
A61K 36/258     (2006.01)
A61K 36/16      (2006.01)
A61K 9/00       (2006.01)
A61K 9/48       (2006.01)
A61K 31/4415    (2006.01)
A61K 31/714     (2006.01)
A61K 31/519     (2006.01)
A23L 33/105     (2016.01)
A23L 33/15      (2016.01)
```
(52) U.S. Cl.
CPC .......... *A61K 36/258* (2013.01); *A23L 33/105* (2016.08); *A23L 33/15* (2016.08); *A61K 9/0053* (2013.01); *A61K 9/48* (2013.01); *A61K 31/4415* (2013.01); *A61K 31/519* (2013.01); *A61K 31/714* (2013.01); *A61K 36/16* (2013.01); *A23V 2002/00* (2013.01)

(58) Field of Classification Search
CPC .................................................. A61K 36/00
See application file for complete search history.

(56) References Cited

U.S. PATENT DOCUMENTS

| | | | |
|---|---|---|---|
| 6,008,221 A | 12/1999 | Smith et al. | |
| 6,083,932 A | 7/2000 | Pang et al. | |
| 6,127,370 A | 10/2000 | Smith et al. | |
| 6,773,729 B2 | 8/2004 | Petrini et al. | |
| 6,964,969 B2 | 11/2005 | McCleary | |
| 8,883,814 B2 | 11/2014 | Reynolds | |
| 9,308,232 B2 | 4/2016 | Reynolds | |
| 9,327,002 B2 | 5/2016 | Reynolds | |
| 9,364,497 B2 | 6/2016 | Smith et al. | |
| 9,498,469 B2 | 11/2016 | Reynolds | |
| 2001/0036484 A1* | 11/2001 | Soldati | A61K 36/16 424/728 |
| 2002/0015744 A1 | 2/2002 | Petrini et al. | |
| 2007/0248696 A1 | 10/2007 | Maletto et al. | |
| 2009/0143433 A1 | 6/2009 | Hendrix | |
| 2013/0034530 A1 | 2/2013 | Fantz | |
| 2016/0038552 A1 | 2/2016 | Bredesen et al. | |

FOREIGN PATENT DOCUMENTS

WO    WO-2008128316 A1 * 10/2008 ............. A61K 36/16

OTHER PUBLICATIONS

Yu et al, Multi-Vitamin B Supplementation Reverses Hypoxia-Induced Tau Hyperphosphorylation and Improves Memory Function in Adult Mice. Journal of Alzheimer's disease: JAD, (Aug. 4, 2016) vol. 54, No. 1, pp. 297-306 (Year: 2016).*

Kobayashi et al, Acetyl-L-carnitine improves aged brain function. Geriatrics & gerontology international, (Jul. 2010) vol. 10 Suppl 1, pp. S99-106 (Year: 2010).*

Reay et al. "Single doses of Panax ginseng (G115) reduce blood glucose levels and improve cognitive performance during sustained mental activity" Journal of Psychopharmacology: 2005, 19(4); pp. 357-365.

Kennedy et al. "Dose Dependent Changes in Cognitive Performance and Mood following Acute Administration of Ginseng to Healthy Young Volunteers" Nutritional Neuroscience: Feb. 2001; pp. 295-310.

Reay et al. "Panax ginseng (G115) improves aspects of working memory performance and subjective ratings of calmness in healthy young adults" Hum. Psychopharmacol Clin Exp: 2010, 25; pp. 462-471.

Sunram-Lea et al. "The Effect of Acute Administration of 400MG of Panax Ginseng on Cognitive Performance and Mood in Healthy Young Volunteers" Current Topics in Nutraceutical Research: 2005, vol. 3, No. 1, pp. 65-74.

Wesnes et al. "The Cognitive, Subjective, and Physical Effects of a Ginkgo biloba/Panax ginseng Combination in Healthy Volunteers With Neurasthenic Complaints" Psychopharmacology Bulletin Health & Medical Complete: 1997, 33, 4; pp. 677-683.

Kennedy et al. "Differential, Dose Dependent Changes in Cognitive Performance Following Acute Administration of a Ginkgo biloba/Panax ginseng Combination to Healthy Young Volunteers" Nutritional Neuroscience: 2001, vol. 4; pp. 399-412.

"Wellbeing and Performance Unilever Health Institute Symposium Series" http://www.academia.edu/2685380/Nutraceuticals_and_Cognitive_Function: 2003; pp. 60.

(Continued)

Primary Examiner — Qiuwen Mi
(74) Attorney, Agent, or Firm — Allen, Dyer, Doppelt + Gilchrist, PA

(57) ABSTRACT

A nutritional supplement composition and associated method enhances working and long term memory support in a healthy adult person, and includes a *Panax Ginseng* extract and *Ginkgo Biloba* extract in a ratio a:b, wherein a for the *Panax Ginseng* extract is between about 1.9 and 2.8 and b for the *Ginkgo Biloba* extract is between bout 0.8 and 1.1. It is formulated for oral administration such that the *Panax Ginseng* extract and *Ginkgo Biloba* extract together account for at least 90 wt % of a dosage unit of the nutritional supplement composition. The *Panax Ginseng* extract and *Ginkgo Biloba* extract together may be present in the amount from about 320 mg to 960 mg. The dosage unit of the composition may be equal to or less than about 1,000 mg.

6 Claims, 2 Drawing Sheets

(56) References Cited

OTHER PUBLICATIONS

Kennedy et al. "Modulation of cognitive performance following single doses of 120 mg Ginkgo biloba extract administered to healthy young volunteers" Hum. Psychopharmacol Clin Exp: 2007, 22; pp. 559-566.
Kennedy et al. "Effects of 8 weeks administration of Korean Panax ginseng extract on the mood and cognitive performance of healthy individuals" J ginseng Res: 2007, vol. 31, No. 1; pp. 34-43.
Kennedy et al. "Electroencephalograph effects of single doses of Ginkgo biloba and Panax ginseng in healthy young volunteers" Pharmacology, Biochemistry and Behavior: 2003, 75 ; pp. 701-709.
Kiesewetter et al. "Hemorrheological and circulatory effects of Gincosan" Int J Clin Pharmacal Ther Toxicol: Mar. 1992, 30(3); pp. 97-102. Abstract Only.
Kennedy et al. "The dose-dependent cognitive effects of acute administration of Ginkgo biloba to healthy young volunteers" Psychopharmacology: 2000, 151; pp. 416-423.
Kennedy et al. "Ginseng: potential for the enhancement of cognitive performance and mood" Pharmacol Biochem Behav: Jun. 2003, 75(3); pp. 687-700. Abstract Only.
Kennedy et al. "Modulation of cognition and mood following administration of single doses of Ginkgo biloba, ginseng, and a ginkgo/ginseng combination to healthy young adults" Physiology & Behavior: 2002, 75; pp. 739-751.
Kennedy et al. "Acute cognitive effects of standardised Ginkgo biloba extract complexed with phosphatidylserine" Hum. Psychopharmacol Clin Exp: 2007, 22; pp. 199-210.
Mahady, GB "Ginkgo biloba for the prevention and treatment of cardiovascular disease: a review of the literature." J Cardiovasc Nurs: Jul. 2002:, 16(4); pp. 21-32. Abstract Only.
Mahadevan et al. "Multifaceted Therapeutic Benefits of *Ginkgo biloba* L: Chemistry, Efficacy, Safety, and Uses" Efficacy, Safety, and Journal of Food Science: 2008, vol. 00, Nr. 0; pp. 6.
Petkov et al. "Effects of standardized ginseng extract on learning, memory and physical capabilities" Am J Chin Med: 1987, 15(1-2); pp. 19-29. Abstact Only.
Petkov et al. "Memory effects of standardized extracts of Panax ginseng (G115), Ginkgo biloba (GK 501) and their combination Gincosan (PHL-00701)" Planta Med: Apr. 1993, 59(2); pp. 106-114. Abstact Only.
McDaniel et al. ""Brain-specific" nutrients: a memory cure?" Nutrition: Nov.-Dec. 2003, 19(11-12); pp. 957-975. Abstract Only.
Mix et al. "A double-blind, placebo-controlled, randomized trial of Ginkgo biloba extract EGb 761 in a sample of cognitively intact older adults: neuropsychological findings." Hum Psychopharmacol: Aug. 2002, 17(6); pp. 267-277. Abstract Only.
Mix et al. "An examination of the efficacy of Ginkgo biloba extract EGb761 on the neuropsychologic functioning of cognitively intact older adults" J Altern Complement Med: Jun. 2000, 6(3); pp. 219-229. Abstract Only.
Moujlton et al. "The effect of Ginkgo biloba on memory in healthy male volunteers" Physiol Behav: Jul. 2001, 73(4); pp. 659-665. Abstract Only.
Nitta et al. Panax ginseng extract improves the scopolamine-induced disruption of 8-arm radial maze performance in rats Bioi Pharm Bull: Oct. 1995, 18(10); pp. 1439-1442. Abstract Only.
Ong et al. "Panax (ginseng)—panacea or placebo? Molecular and cellular basis of its pharmacological activity" Ann Acad Med Singapore: Jan. 2000, 29(1 ); pp. 42-46. Abstract Only.
Persson et al. "The memory-enhancing effects of Ginseng and Ginkgo biloba in healthy volunteers" Psychopharmacology (Berl): Apr. 2004, 172(4); pp. 430-434. Epub Nov. 25, 2003. Abstract Only.
Matsuda et al. "Anti-inflammatory activity of ginsenoside ro" Planta Med: Feb. 1990, 56(1); pp. 19-23. Abstract Only.
McKenna et al "Efficacy, safety, and use of ginkgo biloba in clinical and preclinical applications" Altem Ther Health Med: Sep.-Oct. 2001, 7(5); pp. 70-86, 88-90. Abstract Only.

Schaffler et al. "[Double blind study of the hypoxia protective effect of a standardized Ginkgo biloba preparation after repeated administration in healthy subjects]" Arzneimittelforschunq:1985, 35(8); pp. 1283-1286. Abstract Only.
Scholey et al. The psychopharmacology of herbal extracts: issues and challenges Psychopharmacology: 2005, 179; pp. 705-707.
Sorensen et al. "A Double-Masked Study of the Effects of Ginseng on Cognitive Functions" Current Therapeutic Research: 1996, vol. 57, No. 12; pp. 959-968.
Benishin et al. "Effects of ginsenoside Rb1 on central cholinergic metabolism," Pharmacology: 1991, 42(4); pp. 223-229. Abstract Only.
Chu et al. "New achievements in ginseng research and its future prospects" Chin J Integr Med: Dec. 2009, 15 (6); pp. 403-408. Epub Jan. 18, 2010. Abstract Only.
Cockle et al. "The effects of Ginkgo biloba extract (LI 1370) supplementation on activities of daily living in free living older volunteers: a questionnaire survey" Hum Psychopharmacol: Jun. 2000, 15(4); pp. 227-235. Abstract Only.
Stough et al. "Neuropsychological changes after 30-day Ginkgo biloba administration in healthy participants" International Journal of Neuropsychopharmacology: 2001, 4; pp. 131-134.
Hiai et al. "Evaluation of corticosteron secretion-inducing activities on ginsenosides and their prosapogenins and sapogenins" Chem Pharm Bull: 1983, vol. 31; pp. 168-174.
Salim et al. Ginsenoside Rb1 regulates ChAT, NGF and trkA mRNA expression in the rat brain. Brain Res Mol Brain Res: Jul. 1997, 47(1-2); pp. 177-182. Abstract Only.
Solomon et al. "Ginko for memory enhancement—A randomized controlled trial" JAMA: Aug 21, 2002, vol. 288, No. 7; pp. 835-840.
Weinmann et al. "Effects of Ginkgo biloba in dementia: systematic review and meta-analysis" BMC Geriatrics: 2010, 10:14: pp. 12.
Shipstead et al. "The mechanisms of working memory capacity: Primary memory, secondary memory, and attention control" Journal of Memory and Language: 2014, 72; pp. 116-141.
Abe et al. Differential effects of ginsenoside Rb1 and malonylginsenoside Rb1 on long-term potentiation in the dentate gyrus of rats Brain Res: Jun. 27, 1994; 649(1-2); pp. 7-11. Abstract Only.
Zhao et al. "Ginseng improves strategic learning by normal and brain-damaged rats" Neuroreport: May 11, 1998;9(7): pp. 1619-1624. Abstract Only.
Elsabagh et al. "Differential cognitive effects of Ginkgo biloba after acute and chronic treatment in healthy young volunteers" Psychopharmacology (Berl): May 2005, 179(2); pp. 437-446. Epub Mar. 1, 2005. Abstract Only.
Drago et al. "Pharmacokinetics and bioavailability of a Ginkgo biloba extract." J Ocul Pharmacol Ther: Apr. 2002, 18(2); pp. 197-202. Abstract Only.
D'Angelo "A double-blind, placebo-controlled clinical study on the effect of a standardized ginseng extract on psychomotor performance in healthy volunteers" J Ethnopharmacol: Apr.-May 1986, 16(1); pp. 15-22. Abstract Only.
Ramassamy et al. "Ginkgo biloba extract (EGb 761) in Alzheimer's disease: is there any evidence?" Curr Alzheimer Res: Jul. 2007, 4(3); pp. 253-262. Abstract Only.
Brown et al. "Supplementing cognitive aging: a selective review of the effects of ginkgo biloba and a number of everyday nutritional substances" Experimental Aging Research: 2009, 36; pp. 105-122.
Smith et al. Studies on molecular mechanisms of Ginkgo biloba extract: Appl Microbial Biotechnol: May 2004, 64(4); pp. 465-472. Epub Jan. 22, 2004. Abstract Only.
Rigney et al. "The effects of acute doses of standardized Ginkgo biloba extract on memory and psychomotor performance in volunteers" Phytother Res: Aug. 1999, 13(5); pp. 408-415. Abstract Only.
Wen et al. "Ginseng root prevents learning disability and neuronal loss in gerbils with 5-minute forebrain ischemia." Acta Neuropathol: 1996, 91(1); pp. 15-22.
Birks et al. "Ginkgo biloba for cognitive impairment and dementia" Cochrane Database Syst Rev: Jan. 2009, 21;(1); Abstract Only.
Wesnes et al. "The memory enhancing effects of a Ginkgo biloba/Panax ginseng combination in healthy middle-aged volunteers" Psychopharmacology: 2000, 152; pp. 353-361.

(56) References Cited

OTHER PUBLICATIONS

Wesnes, Keith "The value of assessing cognitive function in drug development" Dialogues in Clinical Neuroscience: 2000, vol. 2 . No. 3; pp. 183-202.
Tildesley et al. "*Salvia lavandulaefolia* (Spanish Sage) enhances memory in healthy young volunteers" Pharmacology, Biochemistry and Behavior: 2003, 75; pp. 669-674.
Scholey et al. "Acute, dose-dependent cognitive effects of Ginkgo biloba, Panax ginsend and their combination in healthy young vounteers: differential interactions with cognitive demand" Hum Psychopharmacol Clin Exp: 2002, 17; pp. 35-44.
Reay et al. "Effects of Panax ginseng, consumed with and without glucose, on blood glucose levels and cognitive performance during sustained 'mentally demanding' tasks" Journal of Psychopharmacology: 2006, 20(6); pp. 771-781.
Hindmarch "Activity of Ginkgo biloba extract on short-term memory" Presse Med: Sep. 25, 1986, 15(31); pp. 1592-1594. Abstract Only.
Warot et al. "Comparative effects of ginkgo biloba extracts on psychomotor performances and memory in healthy subjects" Therapie: Jan.-Feb. 1991, 46(1); pp. 33-36. Abstract Only.
Tachikawa et al. "Effects of ginseng saponins on receptor stimulation-responses" Nihon Yakurigaku Zasshi: Oct. 1997, 110 Suppl 1; pp. 126-131. Abstract Only.
Allain et al. "Effect of two doses of ginkgo biloba extract (EGb 761) on the dual-coding test in elderly subjects" Clin Ther: May Jun. 1993, 15(3); pp. 549-558. Abstract Only.

\* cited by examiner

COMPOSITIONS AND METHODS FOR ENHANCING WORKING AND LONG-TERM MEMORY SUPPORT USING NEW COMBINATION OF GINKGO BILOBA AND PANAX GINSENG AND ASSOCIATED COMPONENTS

FIELD OF THE INVENTION

This invention relates to nutritional supplement compositions and associated methods for administering such compositions, and more particularly, to nutritional supplement compositions and associated methods for enhancing working and long-term memory support.

BACKGROUND OF THE INVENTION

There are numerous approaches known in the art to enhance mood and cognitive performance in normal individuals, including pharmaceutical interventions, aerobic exercise and certain cognitive training programs. Recently, certain nutraceutical agents, such as *Ginkgo Biloba*, and multi-agent compounds have claimed cognitive enhancing effects. Many of those agents and compounds make claims based on their inclusion of one or more individual ingredients whose clinically demonstrated efficacy level(s), or minimal therapeutic threshold amount(s), are typically not achieved in the proposed multi-agent compound or have conflicting clinical trial results.

In some examples, different supplements and formulations include multiple allegedly active ingredients and are marketed as nootropics, or cognitive enhancing agents. For example, the commercially available "Focus Factor" formulation includes over 30 ingredients, while the commercially available "Brain Lightning" formulation has nearly 20 ingredients. Another example disclosed in U.S. Pat. No. 6,964,969 to McCleary lists 47 ingredients with unknown interactions. Any clinical information and cognitive enhancement was only available for individual ingredients and not the combination of so many ingredients. Also, many of those ingredients may interact with one another in a negative manner, lessening the benefits of individual components.

Other marketed formulations include multiple active ingredients with specific effects, and therefore, often suggest that the large number of multiple active ingredients will provide additive, or even synergistic beneficial effects. There have been some clinical trials on some of these formulations and some improvements seen, but results have been mixed. Indeed, the beneficial effects of selected ingredients may individually show cognitive benefits, but when combined together in a specific range may possibly be canceled out by sensory or metabolic overstimulation, while another range of components show promise of beneficial effects. For instance, overstimulation of the cholinergic neurotransmitter system is known to cause receptor desensitization and downregulation of density and may be effected by one range of selected components, but not in another range of selected components or at a specific combination.

A few isolated compounds claiming one or more cognitive effects have been subjected to well controlled (e.g., randomized, double blind, placebo controlled) clinical trials in relatively significant sample sizes (e.g., >50). There have been some clinical trials on *Ginkgo Biloba* extracts and *Panax Ginseng* extracts alone. Researchers and product developers have combined these two components in a very specific 60:100 (3:5) ratio as a composition that is manufactured and sold under the trade name "Gincosan®" by Pharmaton SA. It is a combination of the standardized *Ginkgo Biloba* extract (GK501) as sold by Pharmaton SA and a *Panax Ginseng* extract (G115) as sold by Pharmaton SA in the 60:100 (3:5) ratio, and in typical amounts ranging from about 320 mg to about 960 mg for the total combination.

The 60:100 (3:5) ratio for the *Ginkgo Biloba* and *Panax Ginseng* is very established and almost never deviated from since it is commonly used in almost all commercial applications of the combination of *Ginkgo Biloba* and *Panax Ginseng* and well understood by those skilled in the art. It seems those skilled in the art accept this specific 60:100 (3:5) ratio of *Ginkgo Biloba* and *Panax Ginseng* as "locked in stone" and should not deviate since that is considered the optimum ratio for the combination. This ratio is exclusively used by clinicians and subject to clinical trials and evaluated in published studies such as: 1) Kennedy, D., A. Scholey, and K. Wesnes, Differential, Dose Dependent Changes in Cognitive Performance Following Acute Administration of a *Ginkgo Biloba/Panax Ginseng* Combination to Healthy Young Volunteers; Nutritional Neuroscience, 2001, 4(5): p. 399-412; 2) Wesnes, K., et al., The Memory Enhancing Effects of a *Ginkgo Biloba/Panax Ginseng* Combination in Healthy Middle-Aged Volunteers. Psychopharmacology, 2000, 152(4): p. 353-361; 3) Scholey, A. B. and D. O. Kennedy, Acute, Dose-Dependent Cognitive Effects of *Ginkgo Biloba, Panax Ginseng* and Their Combination in Healthy Young Volunteers: Differential Interactions with Cognitive Demand, Human Psychopharmacology: Clinical and Experimental, 2002, 17(1): p. 35-44; and 4) Kennedy, D., A. Scholey, and K. Wesnes, Modulation of Cognition and Mood Following Administration of Single Doses of *Ginkgo Biloba, Ginseng*, and a Ginkgo/*Ginseng* Combination to Healthy Young Adults, Physiology and Behavior, 2002, 75(5): p. 739-752; the disclosures which are hereby incorporated by reference in their entirety.

Another example of a trial using this well-known 60:100 (3:5) ratio for the *Ginkgo Biloba/Panax Ginseng* composition sold as Gincosan is disclosed in U.S. Pat. No. 6,773,729 to Petrini et al., the disclosure which is hereby incorporated by reference in its entirety. This reference discloses the 60:100 (3:5) combination of *Ginkgo Biloba* and *Panax Ginseng* as Gincosan with no deviation from that ratio and claims the benefit of enhancing the cognitive performance of a healthy child or young adult by the oral administration of 200 to 1,000 mg of this composition.

In an example, 200 to 1,000 mg of this 60:100 (3:5) *Ginkgo Biloba/Panax Ginseng* ratio composition marketed under the tradename Gincosan are administered with the total amount of extract divided up in one to two portions a day such as two dosages, preferably in the morning and at lunch time. The results, especially with the Serial 7s testing, showed the benefits of this composition. All of these studies, however, and numerous other studies using a combination of *Ginkgo Biloba* and *Panax Ginseng*, have been predicated on using the exact ratio for the composition and formulated to deliver typically 200 to 1,000 mg of the composition, which is formulated in the 60:100 (3:5) ratio. The *Ginkgo Biloba* extract contains at least 20% flavone glycosides and typically 2% to 10% terpene lactones and the *Panax Ginseng* extract typically contains at least 3% ginsenosides. This is a very specific 60:100 (3:5) ratio that is basically "set in stone" and rarely deviated from its specific ratio. Those skilled in the art usually do not deviate from that specific ratio when using those two ingredients out of belief the ratio is the best ratio and any change in that ratio may reduce its efficacy.

However, a different ratio may impact and aid to enhance other cognitive functions such as working and long-term memory support. With the mindset that the 60:100 (3:5) ratio can never be deviated from, it becomes difficult to determine if a new ratio and composition range and the addition of additional ingredients to the *Ginkgo Biloba* and *Panax Ginseng* combination is possible.

SUMMARY OF THE INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

The inventor has determined that changing the well-established and almost never deviated from 60:100 (3:5) ratio between the *Ginkgo Biloba* and *Panax Ginseng* is beneficial and has discovered a new formulation as a nutritional supplement composition that enhances working and long-term memory support. This is a surprising result considering that those skilled in the art believe that the 60:100 (3:5) ratio and often specific composition weight are the optimum combination. Also, the inventor has found that his new ratio and combination may include other associated components such as acetyl-L-carnitine and/or a Vitamin B complex to enhance the efficacy of the new composition with its new ratio.

A nutritional supplement composition in accordance with a non-limiting example enhances working and long-term memory support in a healthy young person and includes a *Panax Ginseng* extract and *Ginkgo Biloba* extract in a ratio a:b, wherein a for the *Panax Ginseng* extract is between about 1.9 and 2.8, and b for the *Ginkgo Biloba* extract is between about 0.8 and 1.1. The composition is formulated for oral administration such that the *Panax Ginseng* extract and *Ginkgo Biloba* extract together account for at least 90 wt % of a dosage unit of the nutritional supplement composition.

In an example, the *Ginkgo Biloba* extract is present in the amount from about 90 to about 150 mg. In another example, the *Ginkgo Biloba* extract is present in the amount of about 120 mg. The *Panax Ginseng* extract is present in the amount from about 200 mg to 500 mg and in an example is present in the amount of 250 mg. In yet another example, the *Panax Ginseng* extract and *Ginkgo Biloba* extract together are present in the amount from about 320 to 960 mg. The dosage unit of the composition may be equal or less than about 1,000 mg.

In yet another example, the nutritional supplement composition is formulated into a single dosage capsule. It may include a Vitamin B complex in combination with the *Panax Ginseng* extract and the *Ginkgo Biloba* extract such that the Vitamin B complex is in a ratio between 0.2 and 0.3 with the ratio a:b of the *Panax Ginseng* extract and *Ginkgo Biloba* extract. The Vitamin B complex may be present in the amount from about 25 to 50 mg. The Vitamin B complex may comprise Vitamins B6 and B12 and 5-MTHF.

In yet another example, a nutritional supplement composition enhances working and long-term memory support in a healthy adult person and includes a *Panax Ginseng* extract, a *Ginkgo Biloba* extract and acetyl-L-carnitine in a ratio a:b:c. The a as the *Panax Ginseng* extract is between 1.9 and 2.8, b as the *Ginkgo Biloba* extract is between 0.8 and 1.1, and c as the acetyl-L-carnitine is between 6.0 and 10.0 in non-limiting examples. The composition is formulated for oral administration such that the *Panax Ginseng* extract, *Ginkgo Biloba* extract and acetyl-L-carnitine together account for at least 90 wt % of a new dosage unit of the nutritional supplement composition. The acetyl-L-carnitine may be present in the amount from about 800 to 1,200 mg. The composition may further comprise a Vitamin B complex in combination with *Panax Ginseng* extract, the *Ginkgo Biloba* extract, and acetyl-L-carnitine such that the Vitamin B complex is in a ratio between about 0.2 and 0.3 with the ratio a:b:c of the *Panax Ginseng, Ginkgo Biloba* and acetyl-L-carnitine.

In yet another example, a method for enhancing working and long-term memory support in a healthy adult person comprises administering a nutritional supplement composition that includes a *Panax Ginseng* extract and *Ginkgo Biloba* extract in a ratio a:b, wherein a for the *Panax Ginseng* extract is between about 1.9 and 2.8, and b for the *Ginkgo Biloba* extract is between about 0.8 and 1.1. The method further includes formulating the nutritional supplement composition for oral administration such that the *Panax Ginseng* extract and *Ginkgo Biloba* extract together account for at least 90 wt % of a dosage unit of the nutritional supplement composition.

In yet still another example, a method for enhancing working and long-term memory support in a healthy adult person comprises administering a nutritional supplement composition that includes a *Panax Ginseng* extract, a *Ginkgo Biloba* extract and acetyl-L-carnitine in a ratio a:b:c. A for the *Panax Ginseng* extract is between about 1.9 and 2.8, b for the *Ginkgo Biloba* extract is between about 0.8 and 1.1, and c for the acetyl-L-carnitine is between about 6.0 and 10.0. The method further comprises formulating the nutritional supplement composition for oral administration such that the *Panax Ginseng* extract, the *Ginkgo Biloba* extract, and acetyl-L-carnitine together account for at least 90 wt % of a dosage unit of a nutritional supplement composition.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Figure 1:
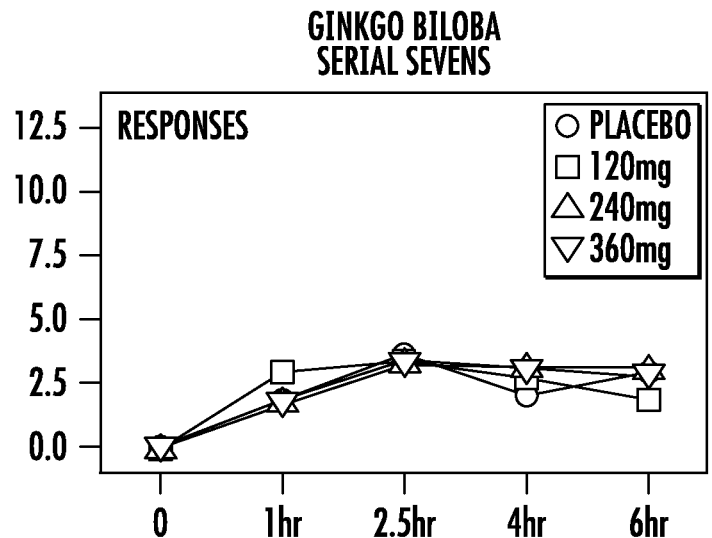
FIG. 1 is a graph showing a Serial Sevens response over the course of a day following single administration of a *Ginkgo Biloba* extract.
Figure 2:
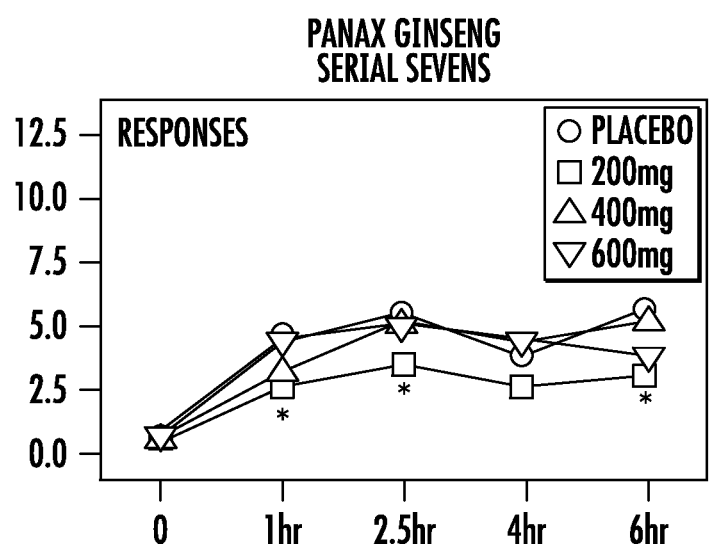
FIG. 2 is a graph showing a Serial Sevens response over the course of a day following single administration of a *Panax Ginseng* extract.
Figure 3:
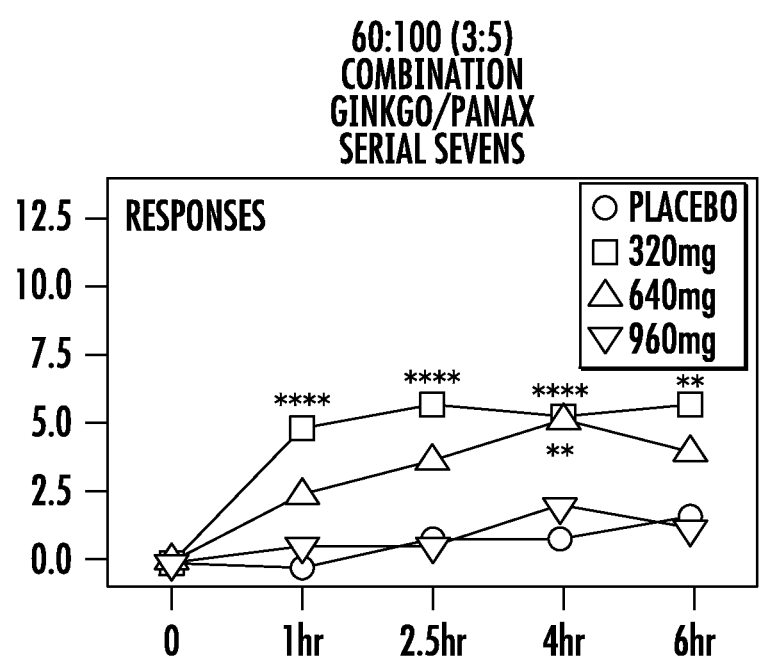
FIG. 3 is graph showing a Serial Sevens response over the course of a day following single administration of a 60:100 (3:5) ratio of *Ginkgo Biloba, Panax Ginseng* and Gincosan.

As noted above, the inventor has found through observation and further development work that the well-known and almost never modified 60:100 (3:5) *Ginkgo Biloba* and *Panax Ginseng* ratio such as described in the above identified articles and in the '729 patent can be unexpectedly and surprisingly modified to enhance working and long-term memory support in a healthy adult person. It is believed that in the field of botanical extracts such as the well-known and almost never modified ratio for Gincosan at 60:100 (3:5) for the *Ginkgo Biloba* extract and *Panax Ginseng* extract, this may be an example where the additive effects of the ingredients are enhanced and not predicted by simply summing the effects of individual components. An example is the combination of the *Ginkgo Biloba* extract and *Panax Ginseng* extract at the conventional and standard 60:100 (3:5) ratio on the performance of the demanding Serial Sevens task that corresponds to the repeated subtraction of 7 from a random three-digit starting number. The effects of the combination of the two are higher than predicted from individual components as noted in FIGS. 1-3 taken from the above-identified '729 patent, where FIG. 1 shows the Serial Sevens for the *Ginkgo Biloba* extract alone and FIG. 2 shows the Serial Sevens result from the *Panax Ginseng* extract alone. FIG. 3 shows the results with the number of responses for the Gincosan 60:100 (3:5) ratio as taken from the '729 patent and described in Scholey et al., 2002 (identified above).

This conventional and almost never deviated from 60:100 (3:5) ratio is understood by those skilled in the art to be integral to the Gincosan composition for many years. The clinical trials in the articles described above and in the '969 patent have all been based on using that ratio with no deviation. Indeed, many of those skilled in the art would never consider abandoning or deviating from that 60:100 (3:5) ratio since a different ratio and different range of composition weight may, in their opinion, cancel out any benefits such as by causing sensory or metabolic overstimulation based upon the changed ratio, for example, overstimulation of the cholinergic neurotransmitter system, which is known to cause receptor desensitization and down regulation of density. Changing the ratio and compositional mass of one of the ingredients relative to the other ingredients may even be a fearful change for those skilled in the art that are used to the specific 60:100 (3:5) ratio. It is almost a mentality that if it is not broken, it does not need fixing. This makes sense in the area of nootropic compositions where adverse effects such as from a changed and well established and conventional ratio, such as the 60:100 (3:5) ratio for Gincosan, may cause harmful effects or be less effective.

The inventor has observed benefits in cognitive function, including enhancements of working and long-term memory, for the new composition when the ratio is changed from the conventional and almost never modified 60:100 (3:5) ratio for the *Ginkgo Biloba* extract and *Panax Ginseng* extract. There appears to be even further enhancement with the addition of other components such as a Vitamin B complex and/or acetyl-L-quantity singularly or in combination. This new composition has been observed to enhance cognitive function and includes working and long-term memory support in a healthy adult person.

The inventor found that the nutritional supplement composition, in accordance with a non-limiting example, may enhance working and long-term memory support in a healthy adult person and includes the *Panax Ginseng* extract and a *Ginkgo Biloba* extract in a ratio a:b, wherein a for the *Panax Ginseng* extract is between about 1.9 and 2.8, and b for the *Ginkgo Biloba* extract is between about 0.8 and 1.1. The composition may be formulated for oral administration such that the *Panax Ginseng* extract and *Ginkgo Biloba* extract together account for at least 90 wt % of the dosage unit of the nutritional supplement composition. Of course, the percentage amount for the *Ginkgo Biloba* extract and *Panax Ginseng* extract as compared to the overall composition may be less when other ingredients such as acetyl-L-carnitine are added and/or larger dosages of a Vitamin B complex are employed. Typically, when a Vitamin B complex is added, the *Panax Ginseng* extract and *Ginkgo Biloba* extract together may account for at least 90 wt % of a dosage unit of the nutritional supplement composition, since typically any Vitamin B complex would be a more negligible amount compared to the combined *Ginkgo Biloba* extract and *Panax Ginseng* extract in the new composition.

In yet another example, the ratio between the *Panax Ginseng* extract and *Ginkgo Biloba* extract may be about 2:1 as compared to the more conventional and clinically tested almost never modified ratio of about 5:3 corresponding to 100 parts per weight of the *Panax Ginseng* extract and 60 parts per weight of the *Ginkgo Biloba* extract. With use of the new composition and modified ratios for *Ginkgo Biloba* and *Panax Ginseng* described above, the inventor has observed what appeared to be an enhanced working and long-term memory support. These ratios may vary. For example, a for the *Panax Ginseng* may vary between about 2.0 and 2.5, and b for the *Ginkgo Biloba* may vary between about 0.9 and 1.0 in an example. These ranges can vary within the overall range of the observed 1.9 and 2.8 for *Panax Ginseng*, and 0.8 and 1.1 for the *Ginkgo Biloba* depending on how the composition is formulated.

In an example, the *Ginkgo Biloba* extract is present in the amount from about 90 to 150 mg and may be present in the amount of about 120 mg in an example. It is possible in some examples to range as high as 240 mg for the *Ginkgo Biloba* extract, but specific amounts could be about 150, 180, 200, 220 or 240 mg for the *Ginkgo Biloba* extract. As long as the new ratio is met as observed by the inventor of "a" between 1.9 and 2.8, and "b" between 0.8 and 1.1, the *Panax Ginseng* extract may be present in the amount from about 200 mg to 500 mg, and in an example, is present in the amount of about 250 mg. That amount can vary and could be about 240 mg, 300 mg, 360 mg, 400 mg, 450 mg, or 500 mg in specific examples for the *Panax Ginseng* extract. In an example, the *Panax Ginseng* extract and *Ginkgo Biloba* extract together may be present in the amount from about 320 mg to 960 mg and the dosage unit of the composition may be equal or less than about 1,000 mg.

The combination of the two ingredients in this new ratio may be present in an amount at 380 mg, 400 mg, 450 mg, 500 mg, 600 mg, 640 mg, 720 mg, 800 mg, 900 mg, or 960 mg as non-limiting examples. Likewise, the composition as a dosage unit in an example is equal to or less than about 1,000 mg, but could be about 1,200 mg, 1,500 mg, 2,000 mg, or 2,500 mg, and may be formulated into a single dosage capsule. It is also possible that a number of capsules can be taken and spread throughout the day or taken at the same time at a specific point in the day such as before an examination.

In another example, it may be possible to add a Vitamin B complex in combination with the *Panax Ginseng* extract and *Ginkgo Biloba* extract, such that the Vitamin B complex in one example is in a ratio between 0.2 and 0.3 with the ratio a:b of the *Panax Ginseng* extract and *Ginkgo Biloba* extract. This ratio can vary, for example, around 0.22 to 0.28 and around 0.25. The Vitamin B complex may be present in the amount from about 25 to 50 mg as non-limiting examples and could be 30 mg, 35 mg, 40 mg, or 45 mg, and even as high as 55 mg. The Vitamin B complex may comprise Vitamins B6 and B12 and 5-MTHF as a non-limiting example. In an example, the Vitamin B6 may be as prixdol 5'-phosphate and may be 20 mg in one example, 30 mg in another example, and 32 mg and up to 50 mg, and in example 50.79 mg. It may be prixdol 5'-phosphate at 63% in an example with corresponding amounts based on that percentage. The Vitamin B12 may be as methylcobalamin and present in the amount of about 0.5 mg (500 mcg), but can vary from 0.25 to 1.0 mg. The 5-MTHF may be from Quatrefolic at 54% (Folate) and be present in an amount of about 0.8 mg (800 mcg) in an example, and up to about 1.5 mg, and in example, 1.481 mg. Other amounts such as 1.0 mg or 1.2 mg may be used.

It is also possible to add acetyl-L-carnitine in a ratio a:b:c, where a as the *Panax Ginseng* extract is between 1.9 and 2.8, b as the *Ginkgo Biloba* extract is between 0.8 and 1.1, and c as the acetyl-L-carnitine is between 6.0 and 10.0 in a non-limiting example. The composition may be formulated for oral administration such that the *Panax Ginseng* extract, *Ginkgo Biloba* extract and acetyl-L-carnitine together account for at least 90 wt % of the dosage unit of the nutritional supplement composition. The *Ginkgo Biloba* extract and *Panax Ginseng* extract may be present in the amounts as noted above while the acetyl-L-carnitine may be present in the amount from about 800 to 1,200 mg, and in another example about 900 to 1,100 mg and in yet another example about 1,000 mg. The composition may be formulated so that the dosage unit of the composition is equal to or less than about 1,200 mg because of the added acetyl-L-carnitine, or may be about 1,500 mg, 2,000 mg, or 2,500 mg and any range therebetween.

There now follows greater details regarding the composition delivery systems that may be employed and a description of additional components such as the acetyl-L-carnitine, Vitamin B complex and yet still other components that may be incorporated within the composition, in accordance with other non-limiting examples. Further details regarding the inventor's observations regarding the efficacy of the composition relative to the more conventional 60:100 ratio between the *Ginkgo Biloba* extract and *Panax Ginseng* extract are also set forth.

Acetyl-L-carnitine in the formulation is thought to increase cerebral energy metabolism by assisting in mitochondrial beta-oxidation and to donate an acetyl moiety for synthesis of acetylcholine. As noted before, optional additional active ingredients may be added, and may include the Vitamin B complex and include folic acid (or Folate), typically in an amount of at least about 0.1 mg (100 mcg) per dosage unit, and more preferably about 0.8 mg (800 mcg) and up to 1 mg per dosage unit. The formulation may possibly also include potassium typically in an amount of at least 10 mg per dosage unit and range up to at least 100 mg per dosage unit or a different range thereof. Furthermore, the composition may include inactive ingredients, which may help in the formulation, disintegration, or other manner. Therefore, suitable inactive ingredients include carriers, binders, excipients, dyes, and similar ingredients. The oral formulation as an example could be in the form of a liquid, powder, gel, or a solid form, and take the form of a tablet, pill, dragee, capsule, or softgel which may or may not have an enteric coating. A coating may allow for the ingredients to bypass the upper GI tract where gastro-intestinal disturbances can be problematic for some individuals. Moreover, one or more of the active ingredients may be formulated in a slow release formulation to extend release over a period of between 1-24 hours. The composition may also be formulated as a liquid or a gel, or embedded in a dissolvable film or chewing preparation.

As noted before, the composition may be formulated such that the daily dosage unit of the composition is equal to or less than 1,000 or 1,200 mg, equal to or less than 1,600 mg, equal to or less than 2,000 mg, and equal to or less than 2,400 mg. The administration may be between once daily and ten times daily depending on the person and amounts used. It may be formed in another example as a single dosage capsule. Suitable oral single dosage forms may have a weight between 200 mg and 600 mg up to 1,000 mg. These amounts can vary. Although the *Panax Ginseng* extract and *Ginkgo Biloba* extract may vary in combined and individual amounts, together they may account for about 90 wt %, but in yet another example could account for at least 80 wt %, but more preferably at least 85 wt %, and even more preferably at least 90 wt %. In some examples, they may at least be about 95 wt % of a dosage unit of the composition. The composition may also include the Vitamin B complex that is added even when acetyl-L-carnitine is added so that together these components account for at least 80 wt %, more preferably at least 85 wt %, even more preferably at least 90 wt %, and up to at least 95 wt % of a dosage unit of the composition.

With respect to marketing such compositions, it is contemplated that the composition may be associated with information regarding the ingredients and its dosages, e.g., printed, displayed, or audio, stating preferably that the nutritional supplement enhances working and long-term memory support in a healthy adult person. It is also possible the composition may improve memory recall capacity and memory recall speed, mental clarity, mental energy, speed of processing, fluid intelligence, and/or mood. These statements may be included on a packaging label. Furthermore, there may be provided an interactive tool (e.g., computer software, link, flash cards, electronic device, etc.) as part of the packaging in an example that allows for testing, training, and/or validation of the cognitive enhancement of the composition or that allows for validation of efficacy of the composition and/or proper personal dosing, or titration to achieve optimal efficacy.

The method as described using the nutritional supplement composition may include a step of providing the composition for oral administration under a schedule and protocol effective to improve cognitive function (with respect to the composition of the supplement, the same considerations as described above apply). Most typically, the cognitive function is a function of one or more types of memory including immediate, short term (a/k/a working memory) and long term (aka episodic, delayed) memory including sensory, procedural, verbal, semantic, numeric, visual, spatial and object learning and recall, a function of memory processing speed, consolidation and retrieval, an aspect of mood, a function of attention (aka focus and concentration), a function of fluid intelligence and processing speed, an executive function, e.g., decision making, multi-tasking (aka task shifting, or switching) and general reasoning. As already pointed out above, the composition may be provided with an interactive tool that allows at least one of validation of efficacy of the composition and proper personal dosing, or titration.

Neuropsychological tests have been employed in trials that use the conventional ratio 60:100 (3:5) Gincosan as described above. Based on these trials, the inventor's observations regarding the beneficial efficacy of the new ratio may be extrapolated.

Different test components as used in trials are described below. (1) The Cognitive Drug Research measure (CDR) is a well-validated test, which is used to assess attention, working memory and episodic secondary (longer term memory, or consolidation). (2) Inspection time (IT) is a measure speed of early information processing. (3) The Profile of Mood States (POMS) is a self-report designed to measure six dimensions of mood: tension-anxiety; depression-dejection; anger-hostility; vigor-activity; fatigue-inertia; and confusion-bewilderment. (4) IQ was assessed using the Raven's Progressive Matrices. This was done by administering the even items at baseline and the odd items at Week 4. (5) The UWIST Mood Adjective Checklist was used to measure mood states and energy levels. (6) The Spielberger State-Trait Anxiety Inventory is a 20-item questionnaire, to measure anxiety at the time of testing. (7) Perceived Stress Scale was used to measure stress symptoms and effective coping.

Without wishing to be bound by any theory or hypothesis, it is contemplated that various factors may have contributed to the inventor's observations of the increased effectiveness of the composition with its changed ratio as compared to the conventional and almost never modified composition ratio 60:100 (3:5) for the *Ginkgo Biloba* extract and *Panax Ginseng* extract. For example, the new composition may stimulate, but not overstimulate, neuro-cognitive brain cell receptors, in effect giving greater processing, but not undermining cognitive function and behavior (e.g., mood). This would be in contrast where a new ratio was in effect a poor ratio between two ingredients or pharmaceutical agents and the poor ratio may cause the composition possibly to overstimulate brain cells, thus down regulating receptor sensitivity and/or density in the corresponding neurotransmitter system, or neuro-cognitive brain area. Downregulation in any neurotransmitter system can cause swift and ultimately debilitating declines in cognitive and/or psychological (mental health) functions, e.g., memory and mood, respectively. The inventor has observed that his new composition with his new ratio does not appear to have any such detrimental effects, but has positive, surprising and beneficial results for enhancing working and long-term memory.

The new composition as described may be referred to as *Procera* Memory Support and includes the *Panax Ginseng* extract and *Ginkgo Biloba* extract in the new ratios as described, but may also include additional mental performance boosting, anti-fatigue and anti-stress ingredients, including the B-Vitamins as a Vitamin B complex as described above, and may also include Vitamins B3 and B5, but more particularly, may include the above described B6, B9 (Folate) and B12. This composition optionally may include a blend of natural sources of caffeine, including a green tea and guarana extract in some cases depending on end uses and need.

The composition with its enhancements may include benefits for improved mental and physical performance under stressful or challenging conditions. The B-vitamin complex and an optional herbal energy boosting extract(s) may support optimal brain function under some peak performance demands besides enhancing working and long-term memory. It has been found that the ingredients and their concentration and ranges may enhance the function of each of the ingredients and may help the brain sustain mental performance longer, including improved concentration, motivation, memory recall and mental energy. The composition may be effective for those persons that require the additional help of greater brain power and mental and physical energy while studying in the classroom, board room or participating in an athletic event.

The composition may include the additional B-Vitamin complex, including Vitamin B6 that has added neurotransmitter support. Added caffeine may be supplied from a guarana seed extract and green tea leaf extract and other natural caffeine sources such as from coffee aribica seeds. The B-Vitamins may support the cholinergic and serotonergic systems. In another example, the composition is formulated with an enteric coating and an inactive ingredient may be selected from the group consisting of a carrier, a binder, an excipient, a dye and combinations thereof. A method of assisting enhancement of cognitive function in a person is also included by administering the nutritional supplement composition.

The example nutritional supplement composition may include Vitamin B3, which is formulated as niacin and niacinamide. The amounts may vary but could correspond to 250% of a daily value such as 50 mg of Vitamin B3 as 25 mg of niacin and 25 mg of niacinamide. The composition in the example may include Vitamin B6 as pyridoxine HCL, and in one example, correspond to a 2,500% daily value such as 50 mg. The composition also may include pantothenic acid as D-calcium pantothenate, and in an example, correspond to 500% of daily value such as 50 mg. The acetyl-L-carnitine is about 1,500 mg per serving.

Caffeine may be provided by the Guarana seed extract that is 22% caffeine in one example. The green tea leaf extract may be 90% caffeine in an example. In another example, the natural caffeine from coffee aribica seeds may be about 90% caffeine. A Guarana seed extract, green tea leaf extract and coffee blend may be about 300 mg, which is equal to about 80 mg of caffeine.

There now follows a description of the various ingredients and their functional workings and relationship. Generally, the composition may work by increasing the circulation of blood to the brain and delivering the oxygen, glucose and other nutrients to increase the brain's energy or cerebral metabolism to improve brain function and cognitive performance. It may also improve key neurotransmitters such as acetylcholine and dopamine to increase sustained focus that is often depleted by stress, sleep loss, poor diet and other physical problems and conditions, including alcohol and aging.

The composition may include the acetyl-L-carnitine (ALC) that is natural to the body and is found in fish, which is one reason fish is called brain food. The human body manufactures some acetyl-L-carnitine, but it declines sharply with age. The signs and symptoms of low acetyl-L-carnitine can be mood swings, memory loss, poor ability to sustain concentration, mental confusion and fatigue. It may be an acetylated form of L-carnitine and is broken down in the blood by plasma esterases to carnitine to transport fatty acids into the mitochondria for breakdown and energy production. The acetyl-L-carnitine and food make the brain more efficient in its energy use.

The B-Vitamin complex may include the Vitamins B6, B9 (Folate) and B12 and possibly may include Vitamins B3 or B5 as described above. These B-Vitamins help sustain sufficient neurotransmitter levels. Some B-Vitamins such as Vitamin B5 as pantothenic acid can be depleted by stress and exhausting mental challenges and raise the need for extra supplementation. The Vitamin B3 may include both niacin and niacinamide. Both may be in equal amounts in one example of the composition if it is used.

Niacin is a derivative of pyridine with a carboxyl group (COOH) at the 3 position and the corresponding niacinamide has the carboxyl group replaced by carboxamide group (CONH) and sometimes other amides and esters. Both niacin and niacinamide are precursors of coenzymes nicotinamide adenine dinucleotide (NAD) and nicotinamide adenine dinucleotide phosphate (NADP). The NAD is important not only in catabolism of fat, carbohydrate, protein and alcohol, but also cell signaling and DNA repair NADP is operative in anabolism reactions and fatty acid and cholesterol synthesis. Its ability to inhibit cyclic adenosine monophosphate (CAMP) production and fat breakdown may also be beneficial in brain function. It is also believed that the niacinamide is an activator of sirtuins to aid in restoring cognition. This could be due to preventing apoptosis in cells exposed to agents that induce oxidative stress, and thus, may prevent apoptosis in neuronal cells.

Vitamin B5 as pantothenic acid may possibly be included and in one example is D-calcium pantothenate to aid in synthesizing coenzyme-A (CoA) and synthesize and metabolize proteins, carbohydrates and fats. The dextrorotatory (D) isomer of pantothenic acid possesses the biologic activity while the levorotatory (L) form may antagonize the effects of the other enantiomer. A racemic mixture is usually not preferred. The coenzyme-A synthesis is beneficial and acts as an acetyl root carrier to form acetyl-CoA to transport carbon atoms within a cell and operates to increase energy metabolism for pyruvate to enter the tricarboxylic acid cycle. It is also important for biosynthesizing acetylcholine.

The Vitamin B6 as pyridoxine HCL may be used for enzymatic reaction governing the release of glucose from glycogen. In vivo, the Vitamin B6 is operative with forming the pyridoxal phosphate-dependent enzymes for biosynethesizing neurotransmitters such as serotonin, dopamine, epinephrine, norepinephrine, and gamma-aminobutyric acid (GABA).

The Vitamin B9 as folic acid may aid in the production of DNA and RNA and work with Vitamins B6 and B12 to control blood levels of the amino acid homocysteine. The amount may vary from as small as 65 mcg to as much as 400 mcg and up to 800 mcg in an example. Vitamin B12 is also water-soluble and may help metabolize cells in the body and effect DNA synthesis, fatty acid and amino acid metabolism. Some of the effects may pertain to the biochemically rare element cobalt that is positioned in the center of the planar tetra-pyrrole ring as a Corrin ring.

As noted before, there may be natural caffeine sources such as the green tea extract and guarana bean extract and natural coffee. Guarana seeds contain about twice the concentration of caffeine found in coffee beans such as 2-4.5% caffeine in guarana seeds as compared to 1-2% in coffee beans. There are many chemicals found in guarana seeds. Primary natural phenols found in guarana include catechin and epicatechin. Catechin is a natural phenol and antioxidant. The catechin and epicatechin are selective monoamine oxidase inhibitors (MAOI) of the type MAO-B and thus may reduce the symptoms of Parkinson's Disease and Alzheimer's patients. Epicatechin is able to cross the blood-brain barrier more efficiently than other agents such as resveratrol, which is more hydrophilic. The catechin may activate BDNF pathways.

Green tea extracts offer additional benefits by obtaining different types of tea catechins, epigallocagethin (EGC), epicatechin gallate (ECG), and epicatechin. There are also different flavonoids such as kaempferol, quercetin, and myricetin. It is more antioxidant active than Vitamin C such as provided by the EGCG. The green tea extracts have better preservation of catechins than black tea extracts and thus are a better anti-inflammatory. Other types of coffee blends may be used although the caffeine content would be less compared to a guarana extract, but would have other components and ingredients that may not be included in the guarana and green tea extracts. About 300 mg of a guarana and green tea extract (with the optional coffee blend) may be used to equal about 80 mg of caffeine.

The ingredients as described for the new composition and the *Panax Ginseng* extract and *Ginkgo Biloba* extract have been selected in their percentage, concentrations and ranges with the overall ratio between the two to operate in the most efficient and best manner as observed by the inventor. These percentages, concentrations, ranges and ratio have been developed using his knowledge, observation and experimentation with known formulations by the inventor and by working with other nootropic formulations such as *Procera AVH* and *Procera XTR* as described in commonly assigned U.S. Pat. Nos. 8,883,814; 9,308,232; 9,498,469; and 9,327,002; the disclosures which are hereby incorporated by reference in their entirety.

It is believed by some researchers that neurotransmitter imbalances cause Alzheimer's Disease because of a reduced synthesis of acetylcholine. The increased NADH as a result of the new composition and possible additional components may result in a six-fold increase in neurotransmitter dopamine and may produce more growth hormone secretion and increase the body's ability to repair or replace damaged and wounded cells. In Parkinson's Disease, the brain cells that produce dopamine die, and thus, the increase in NADH using the composition as described may improve patients that have Parkinson's Disease. The caffeine from the various sources as described may have cognitive enhancing effects on mental energy and enhances the effect of some of the other components and creates vasodilation and enhances the update and use of glucose and oxygen.

The new composition provides enhancements in working and long-term memory and may include some short-term memory such as a factor-derived speed of attention factor and may be achievable with the new composition using the *Panax Ginseng* extract and *Ginkgo Biloba* extract in their new ratios as described, even when the amounts of *Ginkgo Biloba* are reduced from the normally higher amounts evident in some studies for speed of attention to be effective at daily dosages above 240 mg and closer to 360 mg. For example, higher doses of 240 and 360 mg of the *Ginkgo Biloba* extract have been shown to result in improvements on a factor-derived "speed of attention" factor, which was evident at 2.5 hours after ingestion, and was still present at 6.0 hours, i.e., Kennedy et al., "The Dose-Dependent Cognitive Effects of Acute Administration of *Ginkgo Biloba* to Healthy Young Volunteers," *Psychopharmacology*, 2000; 151:416-423. It is believed and based on observations from the inventor that the current composition with its combination of *Panax Ginseng* extract, *Ginkgo Biloba* extract, and optional combination with and acetyl-L-carnitine and/or B Vitamin complex, in the range and concentration as described and with the lower dose of the *Ginkgo biloba* at around 90 to 150 mg and at 120 mg, in an example, interacts with the other components and provides similar results and improvements for a factor derived "speed of attention" matter.

Some published and reported studies involving the beneficial use of *Ginkgo Biloba* have employed generally a minimum of about at least 120 to 240 mg/day, and often much more of *Ginkgo biloba* extract over several months or years. Other similar studies have been found that larger dosages of *Ginkgo Biloba* of at least 320 to 600 mg as a single dosage at one time enhances cognitive performance when a subject is presented briefly the stimuli, for example, large numbers of pictures or words. These studies have confirmed that even the single larger 320 to 600 mg dosage at one time aids in processing and recalling this information rapidly. The current composition with its reduced amount of *Ginkgo Biloba*, e.g., a preferred 120 mg in one example, and using the increased amount of *Panax Ginseng* relative to the more conventional 60:100 ratio for Gincosan and also optionally including acetyl-L-carnitine and/or B Vitamins, is believed to enhance working and long-term memory support in a healthy adult person and possibly aid a subject's cognitive performance when a subject is presented briefly stimuli such as large numbers of pictures or words, but especially may enhance according to observation working and long-term memory support.

In an example, the *Ginkgo Biloba* used in the current composition is a leaf extract having 24% glycosides and 6% terpenes. The *Ginkgo Biloba* could be a standard extract or it could be an extract specifically prepared for use with the acetyl-L-carnitine and/or B Vitamins and other added components.

As noted before, a very well-known and commonly and commercially prepared preparation uses *Ginkgo Biloba* extract in combination with the *Panex Ginseng* extract in the very specific 60:100 (3:5) ratio and commercially sold as Gincosan®. One reason for using the *Ginkgo biloba* extract in combination with *Panex Ginseng* extract in that specific 60:100 (3:5) ratio results from the conventional belief that this particular ratio provides the most efficacious result and the *Ginkgo Biloba* interacts with many other drugs and herbs and has possible side effects and adverse interactions when combined with those drugs and/or herbal compositions, while also possibly losing its effectiveness. Thus, according to belief, only that specific ratio 60:100 (3:5) is effective and preferably those two components are typically used alone with no other ingredients or only with a limited number of other ingredients. However, the inventor found that adverse interactions are apparently minimal using the improved composition and components at his new ratio and concentration ranges, for example, the *Ginkgo Biloba, Panax Ginseng* and optionally acetyl-L-carnitine and/or Vitamin B complex.

As described above, the effective daily dosage may be administered between once daily and four times daily in dosage units of accordingly adjusted weight. Again, the term "about" in conjunction with a numeral may refer to a range of that numeral as plus or minus 10% inclusive.

The *Ginkgo Biloba* extract may be formed as a concentrate and obtained from its leaves whether dried or fresh and prepared in one example using an acetone-water solution. The *Ginkgo biloba* extract is known to have a number of flavonoids and many other natural plant products, many of them containing a series of carbon rings. For example, different flavonoids in the *Ginkgo Biloba* extract may include isorhamnetin, D-glucaric acid, anacardic acid, and kaempterol-3. One positive advantage of combining the *Ginkgo Biloba* extract and the *Panax Ginseng* extract and optionally acetyl-L-carnitine and/or B Vitamin complex in the ratio and concentration ranges for the new composition is that the flavonoids may be better absorbed following ingestion. The half-lives usually are about 3 to 10 hours and any added absorption is beneficial. Bioflavonoids may include amentoflavone, ginkgetin, isoginketine, bilobetin, and terpenes such as diterpenes, for example, ginkgolide A, ginkgolide B, and ginkolide C and the sesquiterpene bilobalide. A standard *Ginkgo biloba* extract used for the composition could be EGb 761, but other extracts of course could be used.

As noted before, some studies using *Ginkgo Biloba* extract alone have employed the generally higher concentration range of at least about a minimum of 240 mg/day and delivered over several months for longer term cognitive benefits. Other studies have used higher ranges above 240 mg, such as 320 mg or 600 mg as single dosages of *Ginkgo biloba* for short-term cognitive benefits, including enhancing speed of attention factors. Those studies using these acute doses at higher concentrations appear to benefit the users for rapid information processing and performance, especially on briefly presented information, and the subjects appear to show better recall of rapidly presented material immediately after the material is presented. One study had subjects taking the *Ginkgo biloba* extract EGb 761 at higher acute dosages of 320 mg or 600 mg and studied a battery of tests given to those subjects. The test results showed an improved performance in the Sternberg short-term memory test for an improvement in the speed of information processing. Another example is the trial reported in Allain et al., "Effects of Two Doses of *Ginkgo Biloba* Extract (EGb 761) on the Dual-Coding Test in Elderly Subjects," *Clin Ther,* 1993 May-June; 15(3):549-58. The inventor has surprisingly observed, however, that the lower amount of 120 mg as a dosage unit and at a preferred range of about 90 mg to about 150 mg of the *Ginkgo biloba* extract in combination with the higher than normal *Panax Ginseng* extract and in a ratio higher than that used with Gincosan, and optionally acetyl-L-carnitine and/or the B Vitamin complex is efficacious and has surprising beneficial results.

There may be many plausible reasons for the efficacy of the modified and new formulation using *Ginkgo Biloba* extract and its *Panax Ginseng* extract in the new modified ratio as compared to the standard and conventional 60:100 (3:5). It is known that the *Ginkgo biloba* extract may stimulate vasodilation and increase cerebral blood flow and lower blood pressure. Plausible reasons exist for the beneficial interaction among the reduced amount of *Ginkgo Biloba* extract with the increased *Panax Ginseng* extract in the modified ratio as explained and which may optionally include acetyl-L-carnitine and possible Vitamin B complex in the ratios and concentration ranges as described.

It should also be understood that the ginkgolide B terpene is a potent antagonist against platelet activity factor and inhibits platelet aggregation, fibrinolysis, and thrombin activity and for that reason, care is often given when employing the *Ginkgo biloba* extract, especially in combination with other components. The interaction of the reduced amount of *Ginkgo Biloba* extract with the increased *Panax Ginseng* extract in the new ratio and optionally other components may enhance speed of memory and with the new composition as described the working and long-term memory enhancement. The composition may have excellent antioxidant properties and may help inhibit or alleviate cell damage caused by free oxygen radicals to the aging process that could also be associated with the neuropathology underlying Alzheimer's Disease. The *Ginkgo Biloba* extract and *Panax Ginseng* extract in the new ratio and ranges and its optional combination with acetyl-L-carnitine and/or Vitamin B complex may help inhibit the activity of the superoxide dismutase and monoamine oxidase as enzymes that may produce free radicals in the brain and body. This new composition may also help scavenge free radicals.

It is also possible the new composition may protect neurons from oxidative stress, e.g., apoptosis and also reduce the toxic effects of cerebral ischemia. The composition may also help reduce the production of arachidonic acid as a toxic byproduct of lipid metabolism. The diterpenes and sesquiterpenes may protect brain tissue against brain injury caused by reduced oxygen or blood flow and work in conjunction with the *Panax Ginseng* extract and optional acetyl-L-carnitine and Vitamin B complex. Even if the flavonoids and bioflavonoids may not pass through the blood-brain barrier easily, their effect with the composition as described may still have antioxidant action. By selecting a particular type of *Ginkgo biloba* extract and/or its processing and preparation, it is possible to manipulate the amount of ginkgolide B and bilobalide and their components to provide neuroprotective and anti-apoptotic effects.

The new composition as the described combination in the new ratio for the *Ginkgo Biloba/Panax Ginseng* may have a positive impact on the forebrain's acetylcholine system and the acetylcholine neurons that absorb choline from the body. Energy-dependent transport processes may be enhanced, for example, by increasing the amount of acetylcholine that is produced. The new composition may possibly increase the glucose use in the frontal and parietal cortex and enhance glucose utilization in the nucleus accumbens and cerebellum. The new composition may also have an indirect action on the neurotransmitter serotonin and act upon the 5HT-1A serotonin receptor. The new composition may possibly reduce stress-induced elevation of glucocorticoid levels. The composition may also enhance release of the neurotransmitter, GABA or gamma-amino butyric acid.

Components in the *Ginkgo Biloba* extract and *Panax Ginseng* extract may also be advantageous when combined in the concentration ranges and ratios and optionally the other components such as acetyl-L-carnitine and Vitamin B complex as described above. For example, the flavonol and flavone glycosides, lactone derivatives such as the ginkolides, the bilide, ascorbic acid, catechin, iron-basic superoxides, 6-hydroxykinuretic acid, protocatechuic acid, shikimic acid, sterols, and vanilic acid may work individually or selectively together. Care is preferably taken when forming the extract so that a minimal amount of the ginkgotoxin (4-O-methoxypyridoxine) is produced. There also may be some interaction among the components to improve blood flow throughout the body and restore some balance between prostacyclin and thromboxane A2 to improve vessel regulation. The new composition may inhibit monoamine oxidase A and B and inhibit the catechol-O-methyl transferase as an enzyme that breaks down adrenergic transmitters while increasing the number of alpha-adrenoreceptors in the brain since those alpha-adrenoreceptors decrease with age. There may be some effect on benzodiazepine receptors and a decrease in glucocorticoid biosynthesis and increased pancreatic beta-cell function with glucose loading. The cyanogenic glycosides may have some antibacterial and antifungal effects.

Even though it is shown by clinical trials that the larger dosages of *Ginkgo Biloba* extract between 300 and 600 mg enhance speed of attention and benefit short term memory in these larger dosages may cause some restlessness, diarrhea, nausea, vomiting and weakness. The lower dosage of *Ginkgo Biloba* of about 90 to 150 mg in combination with the increased amount and ratio with the *Panax Ginseng* extract as compared to the more conventional 60:100 ratio and optionally include acetyl-L-carnitine and/or Vitamin B complex is advantageous and believed the new composition will not produce the above mentioned adverse effects.

The amino acid L-carnitine is known to be produced by the liver and kidneys and transported to the brain and heart. In an example, it is formed from the amino acids lysine and methionine, but the acetyl-L-carnitine is more advantageous because it crosses the blood-brain barrier. In combination with *Ginkgo Biloba* extract and *Panax Ginseng* extract as the new composition and their ratio, the new composition may increase energy production in the mitochondria and boost not only mental energy, but also physical energy, while increasing the neurotransmitters serotonin and norepinephrine. The acetyl-L-carnitine has anti-inflammatory and anti-oxidant properties to protect brain cells from free radical damage and protect them from toxins and oxygen deprivation. It is well known that the aging process affects the energy producing capabilities of mitochondria. The new composition may help alleviate the accumulation of cellular debris and transport fatty acids from the cytosol into the mitochondria within the cell where fats are oxidized to produce ATP. Acetyl-L-carnitine is the acetylated ester of the amino acid L-carnitine and is an endogenous mitochondrial membrane to help maintain the mitochondrial biochemical energetics and lower the increased oxidative stress that results from aging. The acetyl-L-carnitine may operate with the new composition components of the *Ginkgo Biloba* extract and *Panax Ginseng* extract and aid in carrying long-chain fatty acids across the membrane into the mitochondria and across the blood-brain barrier. It may aid in treating or possibly preventing excess oxidative damage. Some acetyl-L-carnitine supplements employed in trials used the larger amounts at around 1.5 to 3.0 grams a day dose. The inventor has found that the reduced amount of the acetyl-L-carnitine in combination with the *Panax Ginseng* extract and *Ginkgo Biloba* with their new ratio for the new composition is beneficial.

The composition may possibly include biotin such as 0.5 mg, as compared to some commercial daily doses of biotin that range from 1.8 mg to 5.0 mg, amounts that were also employed in some biotin trials. The composition may include alpha lipoic acid, such as a reduced amount of 400 mg as compared to some commercially available 600 to 900 mg amounts used in supplements. The chemical structure of biotin is similar to that of alpha lipoic acid and the reduced concentration ranges in the new composition are below what is normally used commercially for those components. The reduced amounts if used in the new composition have less tendency to compete with each other and interfere with their activity in the body, especially since greater amounts of alpha lipoic acid may compete with greater amounts of biotin and interfere with its activity in the body.

Other components such as Huperzine A may possibly be used such as described in the commonly assigned and incorporated by reference patents.

A Vitamin B complex offers advantages. Vitamin B6 is also known as pyridoxine and aids in allowing the body to make different neurotransmitters and aids in normal brain development and function while also helping the body make the hormones serotonin and norepinephrine to influence mood. It may also help make melatonin in the body. The serotonin and norepinephrine aid in transmitting signals to the brain. Vitamin B6 may also aid in forming myelin as a protein layer around nerve cells. Some of the other components in the composition may also aid the active form as pyridoxal 5'-phosphate (PLP) that serves as a coenzyme for different enzyme reactions in amino acid, glucose and lipid metabolism.

The B vitamins may also work in conjunction with a green tea and guarana extract. Green tea may have a thermogenic effect and with the guarana includes catechin and epigallocatechin-3-gallate (EGCG) to aid in energy expenditure, substrate oxidation and help lower blood pressure. It also may aid in reducing the vasoconstrictive effects of caffeine on the brain. The green tea includes the different phytochemicals such as the polyphenols in caffeine.

The green tea extract if used may operate as an antioxidant and as with the similar family grape seed and pine bark extracts, includes polyphenols and flavonoids such as proanthocyanidins. The main proanthocyanidins include catechins, e.g., epigallocatechin gallate (ECGG), as noted above for example, and as found in green tea. The extract may operate as a natural telomerase inhibitor and may regulate blood sugar, reduce triglycerides, and possibly reverse heart disease. It may aid to prevent DNA damage, aid brain health, and serve as an effective monoamine oxidase (MAO) inhibitor.

There now follows a more detailed description of the memory-enhancing composition with respect to the *Panax Ginseng* extract and *Ginkgo Biloba* extract and the evaluation of known clinical trials and give some support for the observations by the inventor that the specific changed ratio of the *Panax Ginseng* extract and *Ginkgo Biloba* extract in the ratio between 1.9 and 2.8 for the *Panax Ginseng* extract and 0.8 and 1.1 for the *Ginkgo Biloba* extract and which is different from the more conventional Gincosan ratio would be beneficial to enhance working and long-term memory support in a healthy adult person.

Mental performance involves the use of memory and attention as part of a larger benefit of alertness and calmness such as part of mood. "Cognitive function" may describe different neurocognitive or brain-mediated mental processes, which permits a person to perceive, evaluate, store, manipulate, and use information from the environment and internal sources such as memory, concepts, thoughts and experience. A person responds to this information as necessary.

Cognitive functions may be clustered into several domains, such as executive functions, memory, attention, perception, psychomotor functions and language. These cognitive domains are divided into more specified functions. For example, memory can be subdivided into: 1) working memory where information is in consciousness; and 2) secondary memory such as long-term memory where information is stored and retrieved later. Attention can be subdivided into selective, focused, divided and sustained attention functions. Executive functions include more complex processes such as reasoning, planning, inhibition, concept formation, evaluation and strategic thinking.

Dispositional or internal factors may influence mental energy and/or cognitive function, i.e., be influenced by situational factors including mood and arousal. Nutritional intervention on these factors may impact cognitive function. Computerized cognitive testing has increased the sensitivity of tests to cognitive change, including enhancement through functional ingredients. As described before, computerized test batteries, including the CDR battery are employed.

Several studies have investigated the acute changes in mood and cognitive performance of *Ginkgo Biloba* extracts and *Panax Ginseng* extracts alone or in combination where the combination is the very conventional and mostly never modified 60:100 ratio composition sold commonly as Gincosan®.

In a first acute trial (Wesnes et al.), 20 healthy young (mean age 20.6 years) volunteers entered a repeated measures, placebo controlled, double-blind, balanced, crossover study. They received 320 mg (120 mg *Ginkgo*/200 mg *Ginseng*), 640 mg (240 mg *Ginkgo*/400 mg *Ginseng*) and 960 mg (360 mg *Ginkgo*/600 mg *Ginseng*) of the *Ginkgo/Ginseng* combination as the standard and conventional Gincosan 60:100 ratio and placebo in a counterbalanced order on four testing days separated by a 7 day washout period. Wesnes, K., et al., The Memory Enhancing Effects of a *Ginkgo Biloba/Panax Ginseng* Combination in Healthy Middle-Aged Volunteers. Psychopharmacology, 2000. 152 (4): p. 353-361.

Participants completed a tailored version of the CDR computerized battery at a pre-dose baseline and thereafter at 1 hour, 2.5 hours, 4 hours and 6 hours post-dose. Results revealed that 960 mg led to significant improvements in 'quality of memory' at 1 hour and 6 hours post-dose, as compared to placebo. When 'quality of memory' is broken down into its component parts: 'working memory' and 'secondary memory' results revealed that there were no significant effects, of any treatment, in comparison to placebo, on 'working memory'. However, "secondary memory" performance was improved following 960 mg at 1 hour, 4 hours and 6 hours post-dose. With regards to attentional performance, the results revealed that 320 mg and 640 mg led to significantly slowed 'speed of attention', in comparison to placebo, at 4 hours and 6 hours (320 mg treatment only) post-dose. Mood was not affected, at any post-dose time point, by any treatment.

In another study, Scholey, A. B. and D. O. Kennedy, Acute, Dose-Dependent Cognitive Effects of *Ginkgo Biloba*, *Panax Ginseng* and Their Combination in Healthy Young Volunteers: Differential Interactions With Cognitive Demand. Human Psychopharmacology: Clinical and Experimental, 2002. 17(1): p. 35-44, it was reported that 640 mg of a *Ginkgo/Ginseng* combination (comprising 240 mg *Ginkgo* and 400 mg *Ginseng*), i.e., the conventional 3:5, 60:100 ratio led to significant speeded performance of the Serial Threes task at the 1 hour, 2.5 hours, 4 hours and 6 hours post-dose.

Similarly, 320 mg (comprised of 120 mg *Ginkgo and* 200 mg *Ginseng*), i.e., again the standard 3:5 and 60:100 ratio led to a significant speed performance at 4 hours post-dose. The most striking results were found when considering the performance of the Serial Seven's task. 320 mg of the combination led to a significant speeded performance, as compared to placebo, at 1 hour, 2.5 hours, 4 hours and 6 hours post-dose and significant improved accuracy at 2.5 hours and 6 hours post-dose. Similarly, 640 mg led to significant speeded performance at 4 hours post-dose and significant improvements in accuracy at 2.5 hours and 6 hours post-dose whereas 960 mg led to significant improved accuracy at 2.5 hours and 6 hours post-dose.

One large controlled study examined the cognitive effects of chronic administration of 320 mg of the conventional G115/GK501 3:5 (60:100) ratio combination administered as two 120 mg doses. Wesnes, K., et al., The Memory Enhancing Effects of a *Ginkgo Biloba/Panax Ginseng* Combination in Healthy Middle-Aged Volunteers. Psychopharmacology, 2000. 152(4): p. 353-361. Quality of memory was improved throughout the trial at 1 hour, 3 hours and 6 hours post-dosing at weeks 0, 4, 8, 12, and following a two week washout. These data suggest that the memory enhancing effects of a *Ginkgo-Ginseng* combination are maintained with chronic dosing.

It is known by those skilled in the art that the 60:100 (3:5) ratio combination of the *Ginkgo Biloba* extract and *Panax Ginseng* extract may have additive effect as compared to individual components in the demanding Serial Sevens tasks where the repeated subtraction of 7 from a random three-digit starting number can be seen in the above-identified FIGS. 1-3 shown, with results for the *Ginkgo Biloba* alone (FIG. 1), *Panax Ginseng* alone (FIG. 2), and the combination of *Ginkgo Biloba* and *Panax Ginseng* at 60:100 ratio (FIG. 3), as taken from Scholey and Kennedy 2002. The conventional ratio was always used as those skilled in the art believed that by changing the ratio some of the effects of the combination may be reversed so that the effects of the combination may be even less than the individual components. The inventor has observed, however, that working and long-term memory support appears enhanced in a healthy adult person when the new composition ratio of between 1.9 and 2.8 for the *Panax Ginseng* and 0.8 and 1.1 for the *Ginkgo Biloba* is used and the composition is at least 90% of the overall composition as compared to the more conventional Gincosan ratio (3:5). The inventor has determined that the new composition and its new ratio also works with the optional additives and components such as the acetyl-L-carnitine and Vitamin B complex and other possible components.

The cognitive effects of *Ginkgo Biloba* extracts has been studied in the context of aging and dementia. Brown, L., L. Riby, and J. Reay, Supplementing Cognitive Aging: A Selective Review of the Effects of *Ginkgo Biloba* and a Number of Everyday Nutritional Substances. Experimental Aging Research, 2010. 36(1): p. 105-122; Weinmann, S., et al., Effects of *Ginkgo biloba* in dementia: systematic review and meta-analysis. BMC geriatrics, 2010. 10(1): p. 14. The *Ginkgo Biloba* extract is an effective nootropic ingredient.

The *Ginkgo Biloba* tree is one of the oldest surviving tree species on earth, leading to its description as a 'living fossil'. Its history of medicinal use in Traditional Chinese Medicine (TCM) goes back thousands of years. One standardized extract is concentrated in a ratio of 1 part extract to 50 part dried leaves and contains an invariant 24% flavone glycosides (quercetin, kaempferol and isorhamnetin) and 6% terpene lactones (2.8-3.4% Ginkgolides A, B and C, and 2.6-3.2% bilobalide). In France and Germany, the *Ginkgo biloba* extract has been prescribed for tinnitus, headache, dizziness, depression, anxiety, confusion, problems with memory and concentration, and other conditions. Smith, J. V. and Y. Luo, Studies on Molecular Mechanisms of *Ginkgo Biloba* Extract. Applied Microbiology and Biotechnology, 2004. 64(4): p. 465-472; Mahady, G. B., *Ginkgo Biloba* for the Prevention and Treatment of Cardiovascular Disease: A Review of the Literature. The Journal of Cardiovascular Nursing, 2002. 16(4): p. 21-32.

*Ginkgo Biloba* extract alone has now become a widely used dietary supplement in the United States and believed to help age-associated cognitive decline and slow the progression of neurodegenerative diseases associated with dementia such as Alzheimer's disease. Those researchers skilled in the art have studied the long-term neuroprotective effects of a *Ginkgo Biloba* extract and proposed a number of mechanisms, including: antioxidant, anti-inflammatory, preservation of mitochondria function/increased ATP production, inhibition of β amyloid formation, reduction in neuron apoptosis, and enhancement of cholinergic transmission. Ramassamy, C., F. Longpre, and Y. Christen, *Ginkgo Biloba* Extract (EGb 761) in Alzheimer's Disease: Is There Any Evidence? Current Alzheimer Research, 2007. 4(3): p. 253-262; Mahadevan, S. and Y. Park, Multifaceted Therapeutic Benefits of *Ginkgo Biloba* L.: Chemistry, Efficacy, Safety, and Uses. Journal of Food Science, 2008. 73(1).

It has been found that it appears that some components in *Ginkgo Biloba* extract reach peak plasma levels within hours of oral administration. For example, some researchers found that Ginkgolide B peaks around 2.25±0.45 hours following oral administration and has an elimination half-life of 4.31±0.49 hours. Drago, F., et al., Pharmacokinetics and Bioavailability of a *Ginkgo Biloba* Extract. Journal of Ocular Pharmacology and Therapeutics, 2002. 18(2): p. 197-202.

This pharmacodynamic profile suggests that any effects should be evident with acute *Ginkgo Biloba* extract administration. Elsabagh, S., et al., Differential Cognitive Effects of *Ginkgo Biloba* After Acute and Chronic Treatment in Healthy Young Volunteers. Psychopharmacology, 2005. 179 (2): p. 437-446; Kennedy, D., A. Scholey, and K. Wesnes, The Dose-Dependent Cognitive Effects of Acute Administration of *Ginkgo Biloba* to Healthy Young Volunteers. Psychopharmacology, 2000. 151(4): p. 416-423; Kennedy, D., A. Scholey, and K. Wesnes, Modulation of Cognition and Mood Following Administration of Single Doses of *Ginkgo Biloba, Ginseng*, and a *Ginkgo/Ginseng* Combination to Healthy Young Adults. Physiology and Behavior, 2002. 75(5): p. 739-752.

Cockle, S., S. Kimber, and I. Hindmarch, The Effects of *Ginkgo Biloba* Extract (LI 1370) Supplementation on Activities of Daily Living in Free Living Older Volunteers: A Questionnaire Survey. Human Psychopharmacology: Clinical and Experimental, 2000. 15(4): p. 227-235, investigated observer and self-rated measures for quality of sleep and mood in a group of 1000 'free-living older volunteers' who received 120 mg *Ginkgo Biloba* extract (LI1370 from Lichtwer Pharma), and compared them to an untreated control group of 4,028 participants self-rated scales at 1, 2, 3 and 4 months following the study, which showed improvements in all three domains for the *Ginkgo Biloba* extract group in comparison to the control group.

Another researcher observed *Ginkgo* related improvements on the Digit Span Backwards, speed on a working memory task, and a delayed auditory verbal learning task, following a 30-day administration of *Ginkgo Biloba* extract or placebo to 50 participants. Stough, C., et al., Neuropsychological Changes After 30-day *Ginkgo Biloba* Administration in Healthy Participants. The International Journal of Neuropsychopharmacology, 2001. 4(2): p. 131-134.

Another researcher reported improved speed of performance on a timed Stroop task in comparison to the placebo. There was an increased speed of performance on three other tasks, in a parallel groups investigation of the effects of six weeks administration of EGb 761 to 40 extract to 'cognitively intact' healthy, older (55-86 years) participants. Mix, J. A. and W. D. Crews Jr, An Examination of the Efficacy of *Ginkgo Biloba* Extract EGb 761 on the Neuropsychologic Functioning of Cognitively Intact Older Adults. The Journal of Alternative and Complementary Medicine, 2000. 6(3): p. 219-229.

Another study found a beneficial effect of *Ginkgo Biloba* extract in healthy older individuals. Mix, J. A. and D. Crews Jr, A Double-Blind, Placebo-Controlled, Randomized Trial of *Ginkgo Biloba* Extract EGb 761® in a Sample of Cognitively Intact Older Adults: Neuropsychological Findings. Human Psychopharmacology: Clinical and Experimental, 2002. 17(6): p. 267-277. The researchers evaluated cognitive performance in 249 healthy, older individuals who were randomized to a *Ginkgo Biloba* extract or placebo. The experimenter gave participants for six weeks 180 mg EGb 761 in three daily doses. Compared to the placebo group, the *Ginkgo* group exhibited better change-from-baseline scores in tests assessing long-term recognition and recall, and in memory for faces.

One randomized, placebo controlled, double-blind, crossover study, involving 8 healthy male adults, showed improvements in complex choice reaction times during hypoxia following 14 days treatment with *Ginkgo Biloba* extract. Schaffler, K. and P. Reeh, Double Blind Study of the Hypoxia Protective Effect of a Standardized *Ginkgo Biloba* Preparation After Repeated Administration in Healthy Subjects. Arzneimittel-Forschung, 1985. 35(8): p. 1283. The results show protection performance deterioration, which may have more relevance to pathological or memory impairment conditions.

Hindmarch, I., Activity of *Ginkgo Biloba* Extract on Short-Term Memory. Presse Medicale (Paris, France: 1983), 1986. 15(31): p. 1592 describes a double-blind, crossover trial involving a small cohort (8) of healthy but younger adult females. Participants received three doses of EGb 761 (120 mg, 240 mg, 600 mg) and placebo, counterbalanced over four test sessions at weekly intervals. No significant results were reported on Critical Flicker Fusion and Choice Reaction Time tests. There was a significant improvement in performance on a working memory scanning task (the Sternberg task). The *Ginkgo* group exhibited faster response times on these test, which increased as test difficulty increased (i.e., 4, 5 or 6 numbers memorized). This effect was, however, restricted to the higher 600 mg dose.

Another researcher examined two-day administration regimens of four doses (120 to 300 mg). Rigney, U., S. Kimber, and I. Hindmarch, The Effects of Acute Doses of Standardized *Ginkgo Biloba* Extract on Memory and Psychomotor Performance in Volunteers. Phytotherapy research, 1999. 13(5): p. 408-415. In this balanced crossover study, thirty one participants, ranging in age from 30 to 59, were administered a battery of tests at baseline and then at hourly intervals over two days (10 am to 9 pm). Performance was improved for reaction times on the Sternberg numeric working memory task as compared to the placebo, and was seen on days one and two for the 120 mg and 300 mg and on day two alone for the 240 mg doses. These improvements were also more marked for the older participants in the study.

There have been other tests as repeated measures, placebo controlled, double blind, balanced, randomized, crossover design. Participants ingested single doses at 120 mg, 240 mg, and 360 mg of a standardized *Ginkgo biloba* extract (Pharmaton GK501) or a placebo on testing days, each separated by a 7-day washout period. Participants also completed a tailored version of the Cognitive Drug Research (CDR) computerized assessment battery at a pre-dose baseline and then at 1 hour, 2.5 hours, 4 hours, and 6 hours post-dose on those testing days. Results were reported for the four 'primary cognitive outcome measures' (quality of memory, speed of memory, speed of attention, and accuracy of attention), and two 'secondary cognitive outcome measures' (working memory and secondary memory) and finally for all individual tasks.

In Kennedy, D., A. Scholey, and K. Wesnes, The Dose-Dependent Cognitive Effects of Acute Administration of *Ginkgo Biloba* to Healthy Young Volunteers. Psychopharmacology, 2000. 151(4): p. 416-423, the researchers reported a significant dose-dependent increase in the 'speed of attention' factor—an aggregate of reaction time scores from three separate attention tasks. This effect was significant for the 240 mg and 360 mg doses at 2.5 hours, 4 hours and 6 hours. The lower 120 mg dose significantly improved performance on a different measure—the 'quality of memory' factor (comprising scores from six memory tasks) at 1 hour and 6 hours.

Another study evaluated the mood and cognitive effects of single doses of *Ginkgo biloba* extract, *Panax Ginseng* extract, and the 60:100 ratio *Ginkgo-Ginseng* combination in 20 (mean age 21.2 years) young, healthy volunteers using a repeated measures, placebo controlled, double blind, randomized, crossover design. Kennedy, D., A. Scholey, and K. Wesnes, Modulation of Cognition and Mood Following Administration of Single Doses of *Ginkgo Biloba, Ginseng*, and a *Ginkgo/Ginseng* Combination to Healthy Young Adults. Physiology and Behavior, 2002. 75(5): p. 739-752. Participants received four treatments: a placebo, 360 mg of *Ginkgo Biloba* extract, 400 mg *Panax Ginseng* extract, and 960 mg of the *Ginkgo-Ginseng* standard 60:100 combination on separate testing days separated by a seven-day washout period. The CDR computerized test battery was employed with two serial subtraction mental arithmetic tasks (Serial Threes and Serial Sevens) and the Bond-Lader visual analogue mood scale. They made assessments at a pre-dose baseline and thereafter at 1 hour, 2.5 hours, 4 hours and 6 hours post-dose. There were significant improvements in 'quality of memory' for all three active doses, in comparison to the placebo. On the *Ginkgo Biloba* extract alone, the improvements were restricted to a single post-dose time point improvement at 6 hours.

In one study comparing the *Ginkgo Biloba* extract (GK501) alone with *Ginkgo Biloba* extract complexed with phosphatidylserine, the *Ginkgo* alone arm had no effect on the CDR cognitive factors. Kennedy, D. O., et al., Acute Cognitive Effects of Standardised *Ginkgo Biloba* Extract Complexed with Phosphatidylserine. Human Psychopharmacology: Clinical and Experimental, 2007. 22(4): p. 199-210. However, it did reduce Choice Reaction Time accuracy at 2.5 hours, 4 hours and 6 hours, and slow the spatial working memory response time at 6 hours.

A reanalysis incorporated the data from that study and two others using similar methodology in which a 120 mg *Ginkgo Biloba* extract was included as one arm. Kennedy, D., et al., Modulation of Cognitive Performance Following Single Doses of 120 mg *Ginkgo Biloba* Extract Administered to Healthy Young Volunteers. Human Psychopharmacology: Clinical and Experimental, 2007. 22(8): p. 559-566. This study revealed that the attentional effects may be less robust than the memory effects. There was some slowing of speed of attention at 1 hour and 6 hours and a trend in the same direction at 4 hours. The 120 mg *Ginkgo Biloba* extract seemed to improve quality of memory at all post-administration time points, especially at 1 and 4 hours following administration, with some trend at 6 hours.

Three studies focused on different aspects of cognitive function as mainly the cognitive load, e.g., the amount of 'mental effort'. Scholey, A. and D. Kennedy, Acute, Dose-Dependent Cognitive Effects of *Ginkgo Biloba, Panax Ginseng* and Their Combination in Healthy Young Volunteers: Differential Interactions with Cognitive Demand. Human Psychopharmacology: Clinical and Experimental, 2002. 17(1): p. 35-44. One of the studies evaluated the effects of three doses (120 mg, 240 mg, 360 mg) of a standardized *Ginkgo Biloba* extract on performance of two related serial subtraction tasks with different levels of mental effort—Serial Threes and Serial Sevens. An assessment occurred at baseline at 1 hour, 2.5 hours, 4 hours, and 6 hours post-treatment. Compared with the placebo, all three dosages of *Ginkgo Biloba* increased the number of Serial Threes completed at 4 hours, and the 240 mg dose also improved performance at 6 hours. Again, this study emphasizes the belief among those skilled in the art for the increased amount of *Ginkgo Biloba* extract alone that is expected for enhancing cognitive function.

One study has investigated electroencephalograph (EEG) effects of single doses of both *Ginkgo biloba* (360 mg GK501) and *Panax Ginseng* (200 mg G115) in 15 (mean age 26.6) healthy young volunteers. Kennedy, D., et al., Topographic EEG Effects of Single Doses of *Panax Ginseng* and *Ginkgo Biloba*. Pharmacology, Biochem and Behav, 2003.

75: p. 701-709. Using a double-blind, placebo-controlled, balanced, crossover design, participants were assessed on three separate occasions at 4 hours post-dose. *Ginkgo*, like *Ginseng*, led to significant reductions in frontal 'eyes closed' theta and beta activity. These effects reflect a higher level of cognitive activity.

There now follows a summary of results on the use of *Panax Ginseng* extract. As known to those skilled in the art, *Ginseng* refers to species of the *Panax* genus of the Araliaceae plant family. *Ginseng* extracts go back years in Traditional Chinese Medicine as a 'tonic' for energy and convalescence aid for the ill and elderly. The effects become more apparent, according to some experts, when a person's resistance is diminished or that person requires extra demands in mind and body. Some evidence shows that individual ginsenosides have anti-inflammatory effects in vivo and in vitro and possess anti-mutagenic and DNA protective properties.

The constituents of the *Panax* genus believed to contribute to its bioactivity are the ginsenoside saponins. Ginsenosides are classified into three groups based on chemical structure: 1) the Panaxadiol group (Rb1, Rb2,Rb3, Rc etc.); 2) the Panaxatriol group (Re, Rf, Rg1, Rg2, Rh1); and 3) the oleanolic acid group (e.g. Ro). A standardized extract G115 (Pharmaton) contains an invariant 4% ginsenosides while Ginsenipure™ (Naturex) is marketed in two forms, standardized to 4% and 15% ginsenosides respectively.

Ginsenosides may impact the cholinergic system, which is critically involved in attention and memory. Isolated Rb1 stimulates choline acetyltransferase activity and acetylcholine release. Ginsenosides Rg1 and Rb1 may alter brain serotonin concentrations, thus influencing mood and sleep. Another target is the nerve growth factor. Rb1 was capable of in vivo modulation of long term potentiation (LTP), which is a putative analogue of memory formation. Other ginsenosides may effect specific cognition-relevant mechanisms. For example, Rd may influence corticosterone secretion and ginsenosides Rd and Re may increase levels of the norepinephrine, dopamine, serotonin and GABA.

In rodents, some studies indicate *Ginseng* may attenuate learning deficits associated with aging or forebrain ischemia, while *Panax Ginseng* was also neuroprotective, rescuing hippocampal neurons. In young rodents, *Ginseng*-related improvements may follow an inverted U dose-response. Mice administered 3, 10, 30, 100 and 300 mg/kg *Panax Ginseng* (extract G115) appeared to improve performance following 10 mg/kg in an inverted-U dose-response manner.

Placebo-controlled, double-blind, balanced, crossover studies employed a computerized assessment battery to investigate the acute behavioral and mood effects of single doses of a standardized *Panax Ginseng* extract. These acute studies identified both positive, and to a lesser extent, negative, cognitive and mood effects of single doses of *Panax Ginseng* as the standardized extract G115 in healthy young adults. Most of the researchers found an improved secondary memory performance following use of G115 alone, and in combination with both *Ginkgo biloba* and guarana (*Paullinia cupana*), especially at a single dose of 400 mg. In one example, both a lower (200 mg) and higher (600 mg) dosage led to a slower performance in some tasks requiring mental attention. Kennedy, D., A. Scholey, and K. Wesnes, Dose Dependent Changes in Cognitive Performance and Mood Following Acute Administration of *Ginseng* to Healthy Young Volunteers. Nutritional Neuroscience, 2001. 4(4): p. 295-310. A 400 mg dose improved accuracy of performing a serial subtraction task, while a 200 mg dose had a modest but significant reduction in the speed of performing the same task. Scholey, A. and D. Kennedy, Acute, Dose-Dependent Cognitive Effects of *Ginkgo Biloba, Panax Ginseng* and Their Combination in Healthy Young Volunteers: Differential Interactions with Cognitive Demand. Human Psychopharmacology: Clinical and Experimental, 2002. 17(1): p. 35-44. This slow down in speed of task performance contrasts with other studies using the same 200 mg dose where there was an improved speed of information retrieval, attention and arithmetical performance, and significantly shortened latency of the P300 component of auditory evoked potentials, Kennedy, D. O., et al., Acute Cognitive Effects of Standardised *Ginkgo Biloba* Extract Complexed with Phosphatidylserine. Human Psychopharmacology: Clinical and Experimental, 2007. 22(4): p. 199-210; Kennedy, D., et al., Modulation of Cognitive Performance Following Single Doses of 120 mg *Ginkgo Biloba* Extract Administered to Healthy Young Volunteers. Human Psychopharmacology: Clinical and Experimental, 2007. 22(8): p. 559-566; Kennedy, D., J. Reay, and A. Scholey, Effects of 8 Weeks Administration of Korean *Panax Ginseng Ginseng* Extract on the Mood and Cognitive Performance of Healthy Individuals. Journal of *Ginseng* Research ( ) 2007. 31(1): p. 34-43. With 400 mg G115, there were some faster responses on an attentional task 90 minutes post-dose. Sünram-Lea, S., et al., The Effect of Acute Administration of 400 mg of *Panax Ginseng* on Cognitive Performance and Mood in Healthy Young Volunteers. Current Topics in Nutraceutical Research, 2004. 3(1): p. 251-254. Additionally a recent report has found better performance on a deliberately demanding cognitive battery coupled with reduced capillary blood glucose (Reay et al, 2006). Reay, J., D. Kennedy, and A. Scholey, Effects of *Panax Ginseng*, Consumed With and Without Glucose, on Blood Glucose Levels and Cognitive Performance During Sustained' Mentally Demanding' Tasks. Journal of Psychopharmacology, 2006. 20(6): p. 771.

Few behavioral studies address the effects on cognition when there is a chronic administration of *Panax Ginseng* extract in humans. One study reported the effects of 12 weeks administration of *Panax Ginseng* (200 mg 6115 per day) on healthy young volunteers' cognitive and psychomotor performance. D'angelo, L., et al., A Double-Blind, Placebo-Controlled Clinical Study on the Effect of a Standardized *Ginseng* Extract on Psychomotor Performance in Healthy Volunteers. Journal of Ethnopharmacology, 1986. 16(1): p. 15-22. Cognitive and psychomotor assessments were conducted at a pre-treatment baseline and then during the 12th week of treatment. There were more correct responses on a mental arithmetic task for those taking the *Panax Ginseng* extract. However, there were few differences between the *Ginseng* and placebo group on a cancellation task. Another study investigated the effects of 8 to 9 weeks use of 400 mg standardized Gerimax™ *Ginseng* extract on cognitive performance in healthy middle aged participants. Sorensen, H. and J. Sonne, A Double-Masked Study of the Effects of *Ginseng* on Cognitive Functions Current Therapeutic Research, 1996. 57(12): p. 959-968. The participants using *Ginseng* had faster performance in a rapid auditory reaction times test (10th percentile).

Another study (N=16) reported positive results after 8 weeks of *Panax Ginseng* use on working memory performance and a reduced self-rated calmness. Kennedy, D., J. Reay, and A. Scholey, Effects of 8 weeks Administration of Korean *Panax Ginseng Ginseng* Extract on the Mood and Cognitive Performance of Healthy Individuals. Journal of *Ginseng* Research ( ) 2007. 31(1): p. 34-43.

In another study, 20 healthy young (mean age 21 years) volunteers participated in a repeated measures, placebo controlled, double blind, balanced, randomized, crossover trial. Kennedy, D., A. Scholey, and K. Wesnes, Dose Dependent Changes in Cognitive Performance and Mood Following Acute Administration of *Ginseng* to Healthy Young Volunteers. Nutritional Neuroscience, 2001. 4(4): p. 295-310. Participants ingested 200 mg, 400 mg, and 600 mg of the *Panax Ginseng* extract on separate days. Each testing day was separated by a 7-day washout period. Participants completed on each testing day a tailored version of the CDR computerized assessment research battery at a pre-dose baseline for 1 hour, 2.5 hours, 4 hours, and 6 hours post-dose. Results were reported for the four "primary cognitive outcome measures" (quality of memory, speed of memory, speed of attention, and accuracy of attention), the two "secondary cognitive outcome measures" (working memory and secondary memory) and finally for all individual tasks. The 200 mg (G115) dose, as compared with placebo, slowed in the 'speed of memory' 4 hour post-dose and showed slowing in 'speed of attention' 4 hour and 6 hour post-dose. However, the same 200 mg dose improved 'accuracy of attention' 6 hour post-dose. The 400 mg dose improved 'quality of memory' at 1 hour, 2.5 hour, 4 hour, and 6 hour post-dose, in comparison to the placebo. The 600 mg improved, as compared to placebo, 'quality of memory' at 2.5 hour. However, the same dose slowed the 'speed of attention' at 4 hours and 6 hours. For the 'secondary outcome measures', there was no significant effects of any dose, at any post-dose testing session, in comparison to the placebo, on 'working memory'. However, the 200 mg (G115) dose led to significant improvements in 'secondary memory' at 4 hour post-dose. Similarly, the 400 mg and 600 mg dosages led to significant improvements in 'secondary memory' performance at 1 hour, 2.5 hours, 4 hours and 6 hours (400 mg only).

Individual tasks such as the simple reaction time, choice reaction time, and digit vigilance reaction time are part of the 'Speed of Attention'. The researchers found that 400 mg and 600 mg (G115) slowed in 'simple reaction time' 4 hour (600 mg only) and 6 hour post-dose, while 200 mg slowed a 'choice reaction time' at 1 hour, 4 hours and 6 hour post-dose. The 200 mg and 600 mg dose slowed the 'Digit Vigilance' test at 4 hours and 6 hours post-dose. Both 200 mg and 600 mg doses had reduced accuracy in performing 'digit vigilance' at 2.5 hours in a post-dose testing session. However, the 400 mg dose resulted in improved accuracy of performing the same task at 1 hour and 4 hour post-dose as compared to the placebo.

As noted before, the Kennedy et al. study investigated the mood and cognitive effects of single dosages of *Ginkgo biloba*, *Panax Ginseng* and the 60:100 ratio *Ginkgo-Ginseng* combination (Gincosan) in 20 (mean age 21.2 years) young, healthy volunteers using the repeated measures, placebo controlled, double blind, randomized, crossover trial. Kennedy, D., A. Scholey, and K. Wesnes, Modulation of Cognition and Mood Following Administration of Single Doses of *Ginkgo Biloba, Ginseng*, and a *Ginkgo/Ginseng* Combination to Healthy Young Adults. Physiology and Behavior, 2002. 75(5): p. 739-752. The 400 mg dose of *Panax Ginseng* improved quality of memory at 1 hour, 2.5 hours, 4 hours, and 6 hours and speed of memory at 4 hours. Quality of memory improved for all three active doses, in comparison to placebo, but restricted to single post-dose time point improvements at 4 hours and 6 hours following *Ginseng* and *Ginkgo* treatments respectively, but improved more for the combination at 1 hour, 2.5 hours, and 4 hours post-dose. Secondary memory improved with *Ginkgo Biloba* extract at 1 hour and 6 hour post-dose with *Panax Ginseng* extract at 4 hour and 6 hour post-dose and at 1 hour and 2.5 hour post-dose for the combination.

The 60:100 (3:5) ratio composition increased the serial three's task 6 hour post-dose whereas the *Ginkgo Biloba* extract improved accuracy 4 hours post-dose, as compared to the placebo. *Ginkgo* and the 60:100 ratio composition speeded performance of the Serial Sevens task for both at 4 hour and 6 hour post-dose for 60:100 ratio composition whereas the *Ginkgo Biloba* extract alone and the 60:100 ratio composition improved accuracy 6 hour post-dose testing.

A similar study was for three separate placebo controlled, double blind balanced crossover trials for *Ginkgo biloba*, *Panax Ginseng* (study 2) and the 60:100 (3:5) composition (study 3) on the performance of Serial Three and Serial Seven subtraction tasks. Scholey, A. and D. Kennedy, Acute, Dose-Dependent Cognitive Effects of *Ginkgo Biloba, Panax Ginseng* and Their Combination in Healthy Young Volunteers: Differential Interactions with Cognitive Demand. Human Psychopharmacology: Clinical and Experimental, 2002. 17(1): p. 35-44. Twenty healthy young volunteers participated in each study. Participants were assessed at a pre-dose baseline and at 1 hour, 2.5 hours, 4 hours and 6 hours post-dose. 200 mg of *Panax Ginseng* extract slowed the Serial Sevens task at 1 hour, 2.5 hours and 6 hours post-dose and an improvement in accuracy at 4 hours. A key distinction is 400 mg of *Panax Ginseng* was associated with significant improvements in accuracy of performing the Serial Sevens task, as compared to the placebo, at 4 hour and 6 hour post-dose.

One study investigated electroencephalograph (EEG) effects of single doses of *Ginkgo biloba* (360 mg GK501) and *Panax Ginseng* (200 mg G115) in 15 (mean age 26.6) healthy young volunteers. Kennedy, D., et al., Topographic EEG Effects of Single Doses of *Panax Ginseng* and *Ginkgo Biloba*. Pharmacology, Biochem and Behav, 2003. 75: p. 701-709. A double-blind, placebo-controlled, balanced, crossover design was used to assess test participants on three separate occasions 4 hours post-dose. The *Panax Ginseng* had a significant shortening of the P300 latency component of auditory evoked potential and the *Panax Ginseng* and *Ginkgo Biloba* led to significant reductions in the frontal 'eyes closed' theta and beta activity, with additional reductions in the alpha waveband for *Panax Ginseng*. 400 mg would have reduced the theta and beta EEG and shortened P300 latency at 4 hours.

In Suram-Lea, S., et al., The Effect of Acute Administration of 400 mg of *Panax Ginseng* on Cognitive Performance and Mood in Healthy Young Volunteers. Current Topics in Nutraceutical Research, 2004. 3(1): p. 251-254, the researchers conducted a placebo controlled, double blind, balanced crossover design for 30 healthy, young (mean age 20 years) participants that received either 400 mg *Panax Ginseng* (G115) or placebo. Participants completed the CDR computerized battery and Bond Lader visual analogue mood scale at a pre-dose baseline and at 90 minutes post-dose. The 400 mg *Panax Ginseng* extract, as compared to the placebo, improved 'speed of attention' 90 minutes post-dose.

In Reay, J., D. Kennedy, and A. Scholey, Single Doses of *Panax Ginseng* (G115) Reduce Blood Glucose Levels and Improve Cognitive Performance During Sustained Mental Activity. Journal of Psychopharmacology, 2005. 19(4): p. 357, the young adults participated in a double-blind, placebo-controlled, crossover study placebo, 200 mg and 400 mg *Panax Ginseng* (G115) were admitted 60 minutes prior to completing six 10-minute cycles of a Cognitive Demand Battery. At 400 mg the researchers noted improved Serial Sevens performance at 60, 70, 80, 90, and 110 minutes and reduced mental fatigue at 70, 80, 90, 100, and 110 minutes.

The inventor had studied extensively these trials as described above and worked diligently to develop the new formulation as described and observed how changing the well-established and almost never deviated from 60:100 (3:5) ratio between the *Ginkgo Biloba* and *Panax Ginseng* is beneficial with his new ratio and dosage. The inventor's new formulation as a nutritional supplement composition enhances working and long-term memory support. The inventor considered this a surprising result considering that those skilled in the art believe that the 60:100 (3:5) ratio and a specific composition dosage are an optimum combination, and for that reason, almost never deviated. Also, the inventor had found that his new ratio may include other associated components, such as the acetyl-L-carnitine and/or Vitamin B complex to enhance the efficacy of the new composition and its new ratio as compared to the established use, composition ratio, and dosage of the Gincosan.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method for enhancing working and long term memory support in a healthy adult person comprising:
   administering a nutritional supplement composition that includes a *Panax Ginseng* extract and *Ginkgo Biloba* extract, wherein said *Panax Ginseng* extract comprises at least 4% ginsenosides and the *Ginkgo biloba* extract comprises a leaf extract comprising about 24% glycosides and 6% terpenes, and the ginsenosides are in the amount of at least 10 mg and are at least 8.3% by weight of the amount by weight of the *Ginkgo biloba* extract, and the *Panax Ginseng* extract is at least 250 mg and the *Ginkgo biloba* extract is at least 120 mg; and
   formulating the nutritional supplement composition for oral administration in a single dosage capsule such that the *Panax Ginseng* extract and *Ginkgo Biloba* extract together account for at least 90 wt % of a dosage unit of the nutritional supplement composition.

2. The method according to claim 1 wherein the *Ginkgo Biloba* extract is present in the amount up to about 150 mg.

3. The method according to claim 2 wherein the *Ginkgo Biloba* extract is present in the amount of about 120 mg.

4. The method according to claim 1 wherein the *Panax Ginseng* extract is present in the amount up to about 500 mg.

5. The method according to claim 4 wherein the *Panax Ginseng* extract is present in the amount of about 250 mg.

6. A method for enhancing working and long term memory support in a healthy adult person comprising:
   administering a nutritional supplement composition that comprises a *Panax Ginseng* extract and *Ginkgo Biloba* extract, wherein said *Panax Ginseng* extract comprises at least about 4% ginsenosides and the *Ginkgo biloba* extract comprises a leaf extract comprising about 24% glycosides and 6% terpenes, and the ginsenosides are in the amount of at least 10 mg and are at least 8.3% by weight of the amount of *Ginkgo biloba* extract, and the *Panax Ginseng* extract is about 250 mg and the *Ginkgo biloba* extract is about 120 mg; and
   formulating the nutritional supplement composition for oral administration into a single dosage capsule such that the *Panax Ginseng* extract and *Ginkgo Biloba* extract together account for at least 95 wt % of a dosage unit of the nutritional supplement composition.

* * * * *